United States Patent
Dadgar

(10) Patent No.: US 11,679,388 B2
(45) Date of Patent: Jun. 20, 2023

(54) CARTRIDGE FOR USE IN A SYSTEM FOR DELIVERY OF A PAYLOAD INTO A CELL

(71) Applicant: SQZ Biotechnologies Company, Watertown, MA (US)

(72) Inventor: Maisam Dadgar, Cambridge, MA (US)

(73) Assignee: SQZ Biotechnologies Company, Watertown, MA (US)

(*) Notice: Subject to any disclaimer, the term of this patent is extended or adjusted under 35 U.S.C. 154(b) by 269 days.

(21) Appl. No.: 16/841,287

(22) Filed: Apr. 6, 2020

(65) Prior Publication Data

US 2020/0316604 A1 Oct. 8, 2020

Related U.S. Application Data

(60) Provisional application No. 62/830,948, filed on Apr. 8, 2019.

(51) Int. Cl.
*B01L 3/00* (2006.01)

(52) U.S. Cl.
CPC ... *B01L 3/502776* (2013.01); *B01L 3/502761* (2013.01); *B01L 2200/10* (2013.01); *B01L 2300/0636* (2013.01); *B01L 2300/0816* (2013.01); *B01L 2300/0829* (2013.01); *B01L 2300/0861* (2013.01)

(58) Field of Classification Search
None
See application file for complete search history.

(56) References Cited

U.S. PATENT DOCUMENTS

| | | | |
|---|---|---|---|
| 4,055,799 A | 10/1977 | Coster | |
| 4,376,634 A | 3/1983 | Prior et al. | |
| 4,835,457 A | 5/1989 | Hanss | |
| 5,023,054 A | 6/1991 | Sato | |

(Continued)

FOREIGN PATENT DOCUMENTS

| CN | 103987836 A | 8/2014 |
|---|---|---|
| JP | H01196566 A | 8/1989 |

(Continued)

OTHER PUBLICATIONS

Adamo, A. et al. (Aug. 7, 2012, e-pub. Jul. 10, 2012). "Microfluidics-Based Assessment of Cell Deformability," Anal Chem 84(15):16438-6443, 13 pages.

(Continued)

*Primary Examiner* — Matthew D Krcha
(74) *Attorney, Agent, or Firm* — Sterne, Kessler, Goldstein & Fox P.L.L.C.

(57) ABSTRACT

A cartridge for delivering a payload to cells of a cell suspension is provided, wherein the cartridge comprises an input channel that delivers the cell suspension to a first plurality of branch channels, and wherein the first plurality of branch channels each deliver the cell suspension into a respective one or a plurality of microfluidic chips or filters. Cell suspension exiting a microfluidic chip or filter flows into a respective one of a second plurality of branch channels, and is then delivered to an output channel by which it exits the cartridge. The cartridge may comprise a plurality of removable covers that hold the chips or filters in place against a body of the cartridge in which the input channel, output channel, and branch channels are formed.

24 Claims, 7 Drawing Sheets

(56) References Cited

U.S. PATENT DOCUMENTS

| | | | |
|---|---|---|---|
| 8,147,867 B2 | 4/2012 | Hong | |
| 8,679,751 B2 | 3/2014 | Huang | |
| 9,364,504 B2 | 6/2016 | Godfrin | |
| 9,458,489 B2 | 10/2016 | Lim | |
| 9,950,049 B2 | 4/2018 | Godfrin | |
| 10,124,336 B2 | 11/2018 | Sharei | |
| 10,526,573 B2 | 1/2020 | Ding | |
| 10,696,944 B2 | 6/2020 | Sharei | |
| 10,780,151 B2 | 9/2020 | Godfrin | |
| 10,870,112 B2 | 12/2020 | Sharei | |
| 2002/0072112 A1* | 6/2002 | Atwood | G05D 23/1917 435/303.1 |
| 2004/0197898 A1 | 10/2004 | Nakatani | |
| 2006/0134067 A1 | 6/2006 | Liu | |
| 2006/0134772 A1 | 6/2006 | Miles | |
| 2006/0263888 A1* | 11/2006 | Fritz | B01L 3/502715 436/63 |
| 2007/0243523 A1 | 10/2007 | Tonescu-zanetti | |
| 2007/0249038 A1 | 10/2007 | Adamo | |
| 2008/0026465 A1 | 1/2008 | Nakata | |
| 2008/0241844 A1 | 10/2008 | Kellogg | |
| 2009/0280518 A1 | 11/2009 | Adamo | |
| 2010/0249621 A1 | 9/2010 | Ichitani | |
| 2011/0030808 A1 | 2/2011 | Chiou | |
| 2011/0275543 A1 | 11/2011 | Deutsch | |
| 2012/0009140 A1 | 1/2012 | Godfrin | |
| 2012/0064518 A1 | 3/2012 | Diefenbach | |
| 2012/0207745 A1 | 8/2012 | Godfrin | |
| 2014/0287509 A1 | 9/2014 | Sharei | |
| 2015/0266022 A1 | 9/2015 | Eltoukhy | |
| 2016/0193605 A1 | 7/2016 | Sharei | |
| 2016/0324946 A1 | 11/2016 | Godfrin | |
| 2018/0003696 A1 | 1/2018 | Sharei | |
| 2018/0016539 A1 | 1/2018 | Ding | |
| 2018/0142198 A1 | 5/2018 | Sharei | |
| 2018/0201889 A1 | 7/2018 | Sharei | |
| 2018/0245089 A1 | 8/2018 | Sharei | |
| 2018/0344822 A1 | 12/2018 | Godfrin | |
| 2018/0361382 A1 | 12/2018 | Zobi | |
| 2019/0017072 A1 | 1/2019 | Ditommaso | |
| 2019/0030536 A1 | 1/2019 | Sharei | |
| 2019/0076847 A1 | 3/2019 | Donovan | |
| 2019/0093073 A1 | 3/2019 | Sharei | |
| 2019/0111082 A1 | 4/2019 | Gilbert | |
| 2019/0382796 A1 | 12/2019 | Gilbert | |
| 2020/0277566 A1 | 9/2020 | Sharei | |
| 2020/0316604 A1 | 10/2020 | Dadgar | |
| 2020/0318066 A1 | 10/2020 | Sharei | |
| 2020/0332243 A1 | 10/2020 | Dadgar et al. | |
| 2021/0038709 A1 | 2/2021 | Loughhead | |
| 2021/0077602 A1 | 3/2021 | Godfrin et al. | |
| 2021/0113628 A1 | 4/2021 | Loughhead et al. | |

FOREIGN PATENT DOCUMENTS

| | | | |
|---|---|---|---|
| JP | H03257366 A | 11/1991 | |
| JP | 2010025852 A | 2/2010 | |
| KR | 20110009422 A | 1/2001 | |
| KR | 100891487 B1 | 4/2009 | |
| KR | 20140134524 A | 11/2014 | |
| RU | 2424792 C2 | 7/2011 | |
| WO | 2006105251 A2 | 10/2006 | |
| WO | 2008021465 A2 | 2/2008 | |
| WO | 2009019317 A1 | 2/2009 | |
| WO | 2010016800 A1 | 2/2010 | |
| WO | 2011051346 A1 | 5/2011 | |
| WO | 2011119492 A2 | 9/2011 | |
| WO | 2013059343 A1 | 4/2013 | |
| WO | 2015023982 A1 | 2/2015 | |
| WO | 2016070136 A1 | 5/2016 | |
| WO | 2016077761 A1 | 5/2016 | |
| WO | 2016115179 A1 | 7/2016 | |
| WO | WO-2016196210 A2 * | 12/2016 | B01L 3/00 |
| WO | 2017008063 A1 | 1/2017 | |
| WO | 2017041050 A1 | 3/2017 | |
| WO | 2017041051 A1 | 3/2017 | |
| WO | 2017070169 A1 | 4/2017 | |
| WO | 2017123663 A1 | 7/2017 | |
| WO | 2017192785 A1 | 11/2017 | |
| WO | 2017192786 A1 | 11/2017 | |
| WO | 2017210334 A1 | 12/2017 | |
| WO | 2017210334 A8 | 3/2018 | |
| WO | 2018039084 A1 | 3/2018 | |
| WO | WO-2018039084 A1 * | 3/2018 | C12M 23/16 |
| WO | 2019113125 A1 | 6/2019 | |
| WO | 2019126212 A1 | 6/2019 | |
| WO | 2019178005 A2 | 9/2019 | |
| WO | 2019178006 A2 | 9/2019 | |
| WO | 2020072833 A1 | 4/2020 | |
| WO | 2020154696 A1 | 7/2020 | |
| WO | 2020176789 A1 | 9/2020 | |

OTHER PUBLICATIONS

American Type Culture Collection (ATCC) (Feb. 27, 2012). "Thawing, Propagating, and Cryopreserving Protocol," Version 1.6, Physical Sciences-Oncology Center Network Bioresource Core Facility, 26 pages.

Anonymous (Jan. 27, 2021). "SQZ Biotechnologies Presents Preclinical Data for their SQZ Tolerizing Antigen Carrier Platform in Antigen-Specific Immune Tolerance (ASIT) Digital Summit Invited Talk," SQZ Biotech. Press Release, 3 pages.

Anonymous (May 18, 2020). "SQZ Biotech Closes $65 Million Series D Financing," SQZ Biotech. Press Release, 2 pages.

Anonymous (Nov. 7, 2019). "SQZ Biotech and AskBio Announce Research Collaboration to Create Immune Tolerization Products for AAV Gene Therapies," AskBio. Press Release, 5 pages.

Anonymous (Oct. 29, 2020). "SQZ Biotech Announces Pricing of Initial Public Offering," SQZ Biotech. Press Release. 2 pages.

Blagovic, K. et al. (Dec. 8, 2020). "Abstract 165—Activating Antigen Carriers Generated With Microfluidics Cell Squeezing Drive Effective Anti-Tumor Responses," JITC, 2 pages.

Bosilkovski, I. (May 21, 2020). "This MIT PhD Just Raised $65 Million for His Clinical Stage Cell Therapy Company," Forbes, retrieved from Internet https://www.forbes.com/sites/igorbosilkovski/2020/05/21/meet-the-mit-phd-who-just-raised-65-million-for-his-clinical-stage-cell-therapy-company/?sh=1e9a48af9809, last visited Mar. 23, 2021, 5 pages.

Chen, C. et al. (2009, e-pub. May 14, 2009). "Patch Clamping on Plane Glass-Fabrication of Hourglass Aperture and High Yield Ion Channel Recording," Lab Chip 9:2370-2380.

Hallow D.M. et al. (Mar. 1, 2008, e-pub. Sep. 18, 2007). "Shear-Induced Intracellular Loading of Cells With Molecules by Controlled Microfluidics," Biotechnology and Bioengineering 99(4):846-854.

Hosokawa, M. et al. (Aug. 1, 2010). "Size-Selective Microcavity Array for Rapid and Efficient Detection of Circulating Tumor Cells", Analytical Chemistry 82(15):6629-6635.

Howarth, M. et al. (May 2008). "Monovalent, Reduced-Size Quantum Dots for Imaging Receptors on Living Cells," Nature Methods 5(5):397-399, 7 pages.

International Preliminary Report on Patentability dated Jun. 23, 2020, for International Patent Application No. PCT/US2018/066295, filed Dec. 18, 2018, 15 pages.

International Search Report and Written Opinion of the International Searching Authority dated Mar. 27, 2020, for International Patent Application No. PCT/US2018/066295, filed Dec. 18, 2018, 23 pages.

International Search Report and Written Opinion, dated Sep. 14, 2020, for PCT Application No. PCT/US2020/026891, filed Apr. 6, 2020, 21 pages.

Invitation to Pay Additional Fees, dated Jul. 23, 2020, for PCT Application No. PCT/US2020/026891, filed Apr. 6, 2020, 14 pages.

Kim, D. et al. (2009, e-pub Apr. 13, 2009). "Microengineered Platforms for Cell Mechanobiology," Annual Review of Biomedical Engineering 11:203-233.

(56) References Cited

OTHER PUBLICATIONS

Lee, J. (Nov. 16, 2012, e-pub. Dec. 2012). "Non-Endocytic Delivery of Functional Engineered Nanoparticles Into the Cytoplasm of Live Cells Using a Novel, High-Throughput Microfluidic Device," Nano Lett. 12 (12):6322-6327, 12 pages.
Liu, W. et al. (Jan. 20, 2010). "Compact Biocompatible Quantum Dots via RAFT—Mediated Synthesis of Imidazole-Based Random Copolymer Ligand," JACS 132(2):472-483, 27 pages.
Liu, Y. et al. (Sep. 19, 2012, e-pub. Jul. 13, 2012). "Spatially Selective Reagent Delivery Into Cancer Cells Using a Two-Layer Microfluidic Culture System," Anal Chim Acta 743(1):125-130, 16 pages.
Matthews, B.D. et al. (2006). "Cellular Adaptation to Mechanical Stress: Role of Integrins, Rho, Cytoskeletal Tension and Mechanosensitive Ion Channels," Journal of Cell Science 119:508-518.
Murphy, J.S. et al. (Sep. 1, 1956, e-pub May 2004). "Measurement of Wall Shearing Stress in the Boundary Layer by Means of an Evaporating Liquid Film," Journal of Applied Physics 27(9):1097-1103, 9 pages.
Ramakrishnan, A. et al. (Jun. 2019). "1743-P: Engineering Erythrocytes with the SQZ Cell Therapy Platform to Enhance Immunotolerance," Diabetes 68(Supplement 1): Poster, 1 page.
Sharei, A. et al. (Feb. 5, 2013, e-pub. Jan. 22, 2013). "A Vector-Free Mircrofuidic platform for Intracellular Delivery", Proc Natl Acad Sci U.S.A. 110(6):2082-2087.
Sharei, A. et al. (Nov. 7, 2013). "Cell Squeezing as a Robust, Microfluidic Intracellular Delivery Platform," Journal of Visualized Experiments (81 ):e50980, 9 pages.
Sharei, A. et al. (Oct. 31, 2012). "(483d) Microfluidic Cell Deformation as a Robust, Vector-Free Method for Cytosolic Delivery of Macromolecules," 12AIChE Proceedings Annual Meeting (https://www.aiche.org/conferences/aiche-annual-meeting/2012/proceeding/paper/483d-microfluidic-cell-deformation-robust-vector-free-method-cytosolic-delivery-macromolecules) last visited on Feb. 4, 2021, 8 pages.
Shelby, J.P. et al. (Dec. 9, 2003). "A Microfluidic Model for Single-Cell Capillary Obstruction by Plasmodium Falciparum-Infected Erythrocytes," PNAS 100(25):14618-14622.
Song, A.Y. et al. (2006). "Scientific Basis for the Use of Hypotonic Solutions with Ultrasonic Liposuction," Aesth. Plast. Surg. 30:233-238, 3 pages.
Tran, J.Q. et al. (Mar. 2021, e-pub. Dec. 16, 2020). "Expansion of Immature, Nucleated Red Blood Cells by Transient Low-Dose Methotrexate Immune Tolerance Induction in Mice," Clin Exp Immunol. 203(2):409-423.
U.S. Appl. No. 16/098,405, filed May 3, 2017, by Loughhead et al. (A copy not submitted herewith pursuant to the waiver of 37 C.F.R. § 1.98(a)(2)(iii) issued by the Office on Sep. 21, 2004.).
U.S. Appl. No. 16/769,993, filed Dec. 4, 2018, by Sharei et al. (Copy not submitted herewith pursuant to the waiver of 37 C.F.R. § 1.98(a)(2)(iii) issued by the Office on Sep. 21, 2004.).
U.S. Appl. No. 17/075,116, filed Oct. 20, 2020, by Sharei et al. (Copy not submitted herewith pursuant to the waiver of 37 C.F.R. § 1.98(a)(2)(iii) issued by the Office on Sep. 21, 2004.).
U.S. Appl. No. 17/169,357, filed Feb. 5, 2021, by Godfrini et al. (Copy not submitted herewith pursuant to the waiver of 37 C.F.R. § 1.98(a)(2)(iii) issued by the Office on Sep. 21, 2004.).
Vinulan, F. (Oct. 12, 2020). "SQZ Biotech Lines Up an IPO on the NYSE to Fund Cell Therapy R&D," Xconomy, retrieved from Internet https://xconomy.com/boston/2020/10/12/sqz-biotech-lines-up-an-ipo-on-the-nyseto-fund-cell-therapy-rd/, last visited Mar. 23, 2021, 3 pages.
Williams, A.R. et al. (Nov. 5, 1999). "Filtroporation: A Simple, Reliable Technique for Transfection and Macromolecular Loading of Cells in Suspension," Biotechnology and Bioengineering 65(3):341-346.
Zarnitsyn, V.G. et al. (2008, e-pub. Nov. 10, 2007). "Electrosonic Ejector Microarray for Drug and Gene Delivery," Biomed Microdevices 10:299-308.

* cited by examiner

CARTRIDGE FOR USE IN A SYSTEM FOR DELIVERY OF A PAYLOAD INTO A CELL

CROSS-REFERENCE TO RELATED APPLICATIONS

This application claims the benefit of U.S. Provisional Application No. 62/830,948, filed Apr. 8, 2019, the entire contents of which are hereby incorporated herein by reference.

FIELD

The present disclosure relates to systems for delivery of a payloads into cells, and more specifically to cartridges for holding constriction-containing elements having constricting channels or constricting pores, for use in tabletop systems for causing perturbations of cell membranes to allow passage of a payload through a cell membrane.

BACKGROUND

The controlled delivery of various materials into cells is important in the developing medical field of cell therapy. For example, various research and therapeutic applications may include the delivery of peptides, nucleic acids, proteins, small molecules, and nanomaterials through cell membranes and into cells. As discussed in WO2013059343, WO2015023982, PCT/US2015/058489, PCT/US2015/060689, and PCT/US2016/13113, constricting microfluidic channels may be used to deliver compounds and other payloads into cells. As disclosed in PCT/US18/66295, tabletop laboratory and/or clinical systems may be configured to force a cell suspension through a constriction cartridge, wherein the constriction cartridge houses one or more constriction-containing elements (e.g., a part, piece, device, component, or the like, such as a microfluidic chip or a filter) having constricting channels or constricting pores, in order to cause perturbations in the membranes of the cells in the cell suspension.

SUMMARY OF THE INVENTION

As explained above, some known systems for intracellular payload delivery include constriction cartridges configured to house one or more constriction-containing elements (e.g., microfluidic chips or filters) having constricting channels or constricting pores, in order to cause perturbations in the membranes of the cells in a cell suspension when the cell suspension flows through the constriction cartridge. However, known systems have non-optimal constriction cartridges, have insufficient constriction cartridge throughput, are susceptible to clogging or failure, are difficult or inefficient to manufacture, and/or house an insufficient number of constriction-containing elements (e.g. chips or filters) therein. Accordingly, there is a need for constriction cartridges that have improved geometric configurations, improved throughput, improved resistance to clogging or other failure, improved ease and efficiency of manufacture, and/or increased constriction-containing element capacity. The systems, methods, and techniques disclosed herein may address one or more of these needs to improve the geometric configurations, throughput, resistance to clogging or other failure, ease and efficiency of manufacture, and capacity of constriction cartridges.

Disclosed herein are cartridges for use in systems for delivering a payload to a cell in a cell suspension. The cartridges may be configured to house a plurality of constriction-containing elements (e.g., chips containing microfluidic channels and/or filters containing pores) through which a cell suspension may be forced, the constriction-containing elements comprising one or more constrictions (e.g., constricting channels or constricting pores) configured to perturb membranes of cells in the cell suspension in order to allow entry of the payload into the cells. The cartridges may be configured to be fluidly connectable to the system for delivery of a payload to a cell, and to form a fluid flow path through which the cell suspension may flow while inside the cartridge. In some embodiments, cell suspension may flow through an input channel and an output channel each formed in a body of the cartridge, the input channel and output channel each intersected by a plurality of branch channels to direct flow (e.g., in parallel) to the plurality of constriction-containing elements. In some embodiments, cell suspension may flow through an input chamber and an output chamber each formed in a body of the cartridge, the input chamber and output chamber each intersected by a plurality of branch channels to direct flow (e.g., in parallel) to the plurality of constriction-containing elements. In some embodiments, an input port and/or output port may be formed on the cartridge body. In some embodiments, an input port and/or output port may be formed on one of a plurality of removable covers configured to be attachable to the cartridge and to hold a plurality of the constriction-containing elements in place against the cartridge body.

In some embodiments, a first cartridge for delivering a payload to cells of a cell suspension is provided, the first cartridge comprising: an input port configured to be fluidly connected to receive flow of the cell suspension; a cartridge body comprising a first surface, the first surface configured to receive a first plurality of constriction-containing elements, each of the first plurality of constriction-containing elements comprising a respective constriction configured to perturb membranes of cells of the cell suspension to facilitate delivery of the payload to the cells; an input channel formed in the cartridge body and configured to fluidly connect the input port to a first plurality of branch channels, wherein each of the first plurality of branch channels connects to the input channel and opens at a respective one of a first plurality of openings to the first surface of the cartridge body; and an output channel formed in the cartridge body, separate from the input channel, and configured to fluidly connect an output port to a second plurality of branch channels, wherein each of the second plurality of branch channels connects to the output channel and opens at a respective one of a second plurality of openings to the first surface of the cartridge body.

In some embodiments of the first cartridge, the first plurality of branch channels and the second plurality of branch channels are oriented in a direction perpendicular to the input channel and the output channel.

In some embodiments of the first cartridge, the first plurality of branch channels and the second plurality of branch channels are associated with one another in pairs of corresponding branch channels, such that fluid may flow from one branch channel of a pair through a constriction-containing element and into another branch channel of the same pair.

In some embodiments of the first cartridge, the branch channels of one or more of the pairs of corresponding branch channels are spaced apart from one another in a direction perpendicular to the input channel and the output channel and perpendicular to the direction of flow of fluid in the branch channels.

In some embodiments of the first cartridge, the first cartridge comprises a first removable cover configured to hold the first plurality of constriction-containing elements in place against the first surface of the cartridge body, wherein the first removable cover is removable to facilitate removal or replacement of the first plurality of constriction-containing elements.

In some embodiments of the first cartridge, the first removable cover is configured to attach to the cartridge body via a sliding connection, such that the first removable cover slides over the first plurality of constriction-containing elements as it is attached to the cartridge body.

In some embodiments of the first cartridge, the first removable cover is configured to slide in a direction parallel to the input channel and the output channel.

In some embodiments of the first cartridge, the first removable cover is configured to slide in a direction perpendicular to the first plurality of branch channels and the second plurality of branch channels.

In some embodiments of the first cartridge, each opening of the first plurality of openings and second plurality of openings is formed in a respective one of a first plurality of recessed cavities formed on the first surface of the cartridge body.

In some embodiments of the first cartridge, the first cartridge comprises a first plurality of compressible o-rings each configured to be retained inside a respective one of the first plurality of recessed cavities, and each configured to form a fluid seal pathway between the an opening of a branch channel in the cartridge body and an opening in a respective one of the first plurality of constriction-containing elements.

In some embodiments of the first cartridge, the input port and the output port are disposed on a same surface of the cartridge body.

In some embodiments of the first cartridge, the first cartridge comprises an additional port, distinct from the input port and output port, fluidly connected to one of the input channel and the output channel.

In some embodiments of the first cartridge, the additional port is sealed by a cap.

In some embodiments of the first cartridge, one of the input channel and the output channel has a diameter of less than 4 mm.

In some embodiments of the first cartridge, one of the input channel and the output channel has a length of less than 15 cm.

In some embodiments of the first cartridge, one of the branch channels has a diameter of less than 4 mm.

In some embodiments of the first cartridge, one of the branch channels has a length of less than 25 mm.

In some embodiments of the first cartridge, the first plurality of branch channels and the second plurality of branch channels each comprise more than four branch channels.

In some embodiments of the first cartridge, the cartridge has an overall fluid throughput of greater than 1 L/min.

In some embodiments of the first cartridge, the cartridge has a length of less than 15 cm.

In some embodiments of the first cartridge, one or more of the first plurality of constriction-containing elements has a length of less than 50 mm.

In some embodiments of the first cartridge, the cartridge comprises one or more of polycarbonate, polypropylene, and polymethyl methacrylate.

In some embodiments of the first cartridge: the cartridge body comprises a second surface, the second surface configured to receive a second plurality of constriction-containing elements, each of the second plurality of constriction-containing elements comprising a constriction configured to perturb membranes of cells of the cell suspension to facilitate delivery of the payload to the cells; each of the first plurality of branch channels opens at a respective one of a third plurality of openings to the second surface of the cartridge body; and each of the second plurality of branch channels opens at a respective one of a fourth plurality of openings to the second surface of the cartridge body.

In some embodiments of the first cartridge, the first cartridge comprises a second removable cover configured to hold the second plurality of constriction-containing elements in place against the second surface of the cartridge body, wherein the second removable cover is removable to facilitate removal or replacement of the second plurality of constriction-containing elements.

In some embodiments, a second cartridge for delivering a payload to cells of a cell suspension is provided, the cartridge second comprising: a cartridge body comprising a first surface configured to receive a first plurality of constriction-containing elements and a second surface configured to receive a second plurality of constriction-containing elements, each of the first plurality of constriction-containing elements and the second plurality of constriction-containing elements comprising a respective constriction configured to perturb membranes of cells of the cell suspension to facilitate delivery of the payload to the cells; a first removable cover configured to hold the first plurality of constriction-containing elements in place against the first surface of the cartridge body and to hold the second plurality of constriction-containing elements in place against the second surface of the cartridge body, wherein the first removable cover comprises an input port configured to receive flow of a cell suspension; and a second removable cover configured to hold the first plurality of constriction-containing elements in place against the first surface of the cartridge body and to hold the second plurality of constriction-containing elements in place against the second surface of the cartridge body, wherein the second removable cover comprises an output port configured to direct flow of the cell suspension out of the cartridge.

In some embodiments of the second cartridge, the first removable cover and the second removable cover are each slidable over the cartridge body, the first plurality of constriction-containing elements, and the second plurality of constriction-containing elements.

In some embodiments of the second cartridge, the first removable cover and the second removable cover are slidable onto and off of the cartridge body in opposed directions.

In some embodiments of the second cartridge, the first removable cover and the second removable cover are each configured to encircle the cartridge body.

In some embodiments of the second cartridge, the cartridge body comprises: an input chamber formed in the cartridge body and opening toward a first side of the cartridge body to which the first removable cover attaches, wherein the input chamber is configured to be fluidly connected to and receive flow of the cell suspension from the input port; and an output chamber formed in the cartridge body and opening toward a second side of the cartridge body to which the second removable cover attaches, wherein the output chamber is configured to be fluidly connected to and direct flow of the cell suspension to the output port.

In some embodiments of the second cartridge, the cartridge body comprises: a first plurality of branch channels, wherein each of the first plurality of branch channels intersects the input chamber and opens at a respective one of a first plurality of openings to the first surface of the cartridge body and at a second plurality of openings to the second surface of the cartridge body; and a second plurality of branch channels, wherein each of the second plurality of branch channels intersects the output chamber and opens at a respective one of a third plurality of openings to the first surface of the cartridge body and at a fourth plurality of openings to the second surface of the cartridge body.

In some embodiments of the second cartridge, the first removable cover and second removable cover are configured to slide in a direction perpendicular to the first plurality of branch channels and the second plurality of branch channels.

In some embodiments of the second cartridge, the first plurality of branch channels and the second plurality of branch channels are associated with one another in pairs of corresponding branch channels, such that fluid may flow from one branch channel of a pair through a constriction-containing element and into another branch channel of the same pair.

In some embodiments of the second cartridge, the branch channels of one or more of the pairs of corresponding branch channels are spaced apart from one another in a direction perpendicular to the direction of flow in the input port and output port and perpendicular to the direction of flow of fluid in the branch channels.

In some embodiments of the second cartridge: each of the first and second pluralities of openings is formed in a respective one of a first plurality of recessed cavities formed on the first surface of the cartridge body; and each of the third and fourth pluralities of openings is formed in a respective one of a second plurality of recessed cavities formed on the first surface of the cartridge body.

In some embodiments of the second cartridge, the cartridge body comprises: a first raised lip configured to form a seal against an inside surface of the first removable cover; and a second raised lip configured to form a seal against an inside surface of the second removable cover.

In some embodiments of the second cartridge: the first raised lip is configured to retain a first o-ring in a first ridge; and the second raised lip is configured to retain a second o-ring in a second ridge.

In some embodiments of the second cartridge: the first raised lip encircles an opening of the input chamber; and the second raised lip encircles an opening of the output chamber.

In some embodiments of the second cartridge, one of the input chamber and the output chamber has a width of less than 5 mm.

In some embodiments of the second cartridge, one of the branch channels has a diameter of less than 4 mm.

In some embodiments of the second cartridge, one of the branch channels has a length of less than 25 mm.

In some embodiments of the second cartridge, the first plurality of branch channels and the second plurality of branch channels each comprise more than four branch channels.

In some embodiments of the second cartridge, the cartridge has an overall fluid throughput of greater than 1 L/min.

In some embodiments of the second cartridge, the cartridge has a length of less than 15 cm.

In some embodiments of the second cartridge, one or more of the first plurality of constriction-containing elements has a length of less than 50 mm.

In some embodiments of the second cartridge, the cartridge comprises one or more of polycarbonate, polypropylene, and polymethyl methacrylate.

In some embodiments, any one or more of the features, characteristics, or elements discussed above with respect to any of the embodiments may be incorporated into any of the other embodiments mentioned above or described elsewhere herein. In some embodiments, any one or more of the features, characteristics, or elements discussed elsewhere in this disclosure may be incorporated into any one or more of the embodiments mentioned above.

BRIEF DESCRIPTION OF THE DRAWINGS

FIG. 2A illustrates an exploded view of the constriction cartridge, in accordance with some embodiments; FIG. 2B illustrates a cross-sectional view of a body of the constriction cartridge, in accordance with some embodiments; and FIG. 2C illustrates a partially transparent view of the constriction cartridge, in accordance with some embodiments.

FIG. 3A illustrates an exploded view of the constriction cartridge, in accordance with some embodiments; FIG. 3B illustrates a partial cross-sectional view of a body of the constriction cartridge, in accordance with some embodiments; and FIG. 3C illustrates a partially transparent view of the constriction cartridge, in accordance with some embodiments.

DETAILED DESCRIPTION OF THE INVENTION

Figure 1:
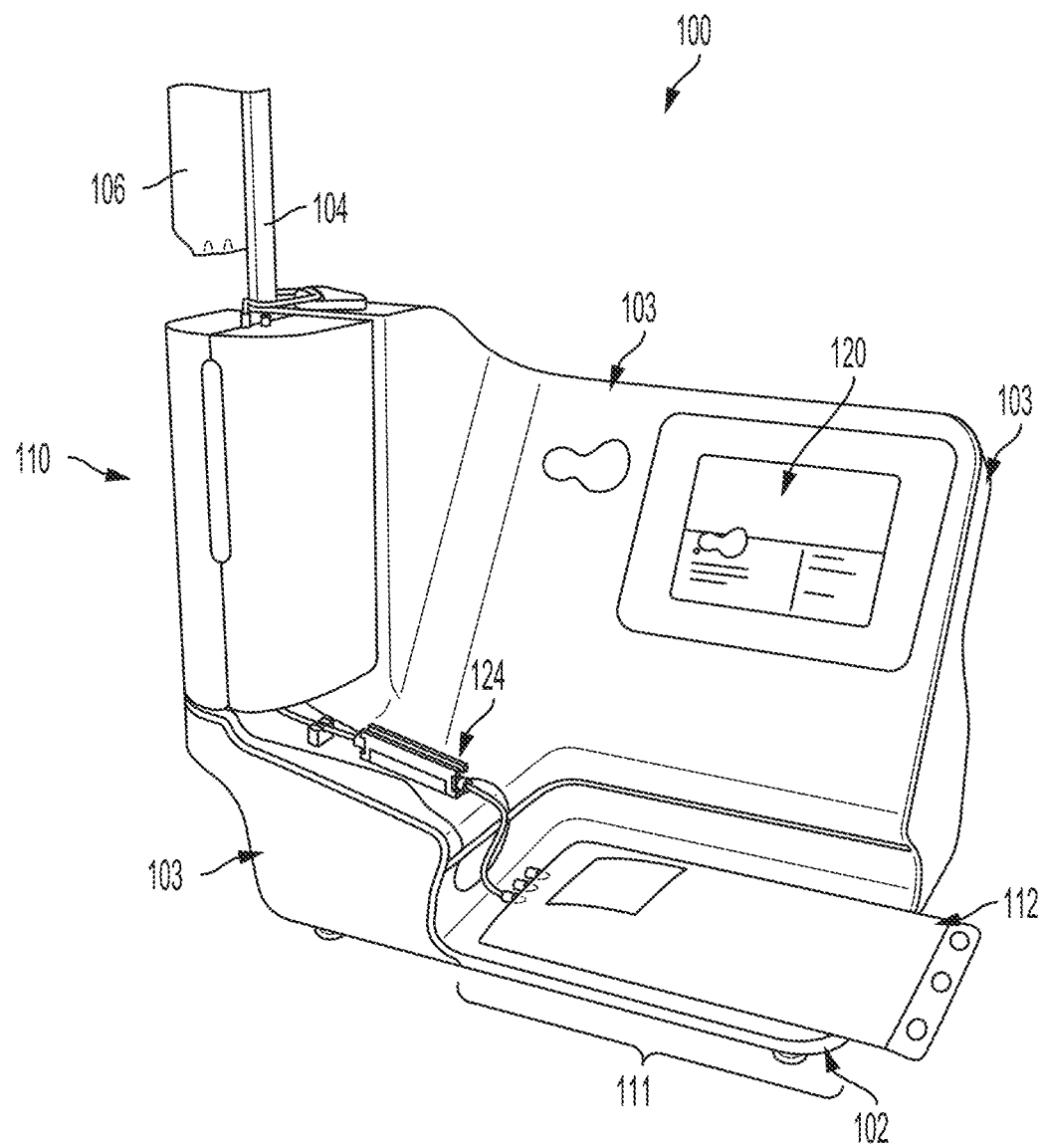
FIG. 1 illustrates a tabletop system for delivering a payload to a cell, in accordance with some embodiments.

Described below are exemplary embodiments of cartridges for use in systems for partially or fully automated intracellular payload delivery, as well as associated devices, systems, methods, and techniques.

Below, the description of FIG. 1 describes an exemplary embodiment of a tabletop system for intracellular payload delivery. The system shown in FIG. 1 may, in some embodiments, share any one or more characteristics with any one of the systems described in PCT/US18/66295, the entire contents of which are hereby incorporated by reference. After that, the description of FIGS. 2A-2C and 3A-3C describes exemplary embodiments of cartridges for use in systems for partially or fully automated intracellular payload delivery. As described below, the cartridges described with reference to FIGS. 2A-2C and 3A-3C may, in some embodiments, be used in systems such as the systems described with reference to FIG. 1.

The following description sets forth exemplary systems, methods, techniques, parameters, and the like. It should be recognized, however, that such description is not intended as a limitation on the scope of the present disclosure but is instead provided as a description of exemplary embodiments.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is further understood that the terms "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The term "about" as used herein refers to the usual error range for the respective value readily known to the skilled person in this technical field. Reference to "about" a value or parameter herein includes (and describes) embodiments that are directed to that value or parameter per se.

The term "pore" as used herein refers to an opening, including without limitation, a hole, tear, cavity, aperture, break, gap, or perforation within a material. In some examples, (where indicated and/or where it would be clear, in light of the disclosure, to a person of skill in the art) the term refers to a pore within a surface of the present disclosure. In other examples, (where indicated and/or where it would be clear, in light of the disclosure, to a person of skill in the art) a pore can refer to a pore in a cell membrane.

The term "filter" as used herein refers to a porous article that allows selective passage through the pores. In some examples the term refers to a surface or membrane containing pores.

Although the description herein uses terms first, second, etc. to describe various elements, these elements should not be limited by the terms. These terms are only used to distinguish one element from another.

For any of the structural and functional characteristics described herein, methods of determining these characteristics are known in the art.

All references cited herein, including patent applications and publications, are incorporated by reference in their entirety.

Constriction Cartridges for use in Intracellular Payload Delivery Systems

FIG. 1 shows intracellular payload delivery system 100. In some embodiments, system 100 may share any one or more characteristics with any one of the systems described in PCT/US18/66295. The features of intracellular payload delivery systems and devices, such as system 100, are described more fully in PCT/US18/66295. In short, an intracellular payload delivery system may enable the delivery of a payload into cells by forcing the cells to flow through a constriction such as a narrow microfluidic channel or a narrow pore, thereby perturbing the membranes of the cells and allowing the payload to enter the cells.

In some embodiments, constrictions such as narrow microfluidic channels or narrow pores may be provided in microfluidic chips or filters, which may be attached in fluid communication to an intracellular payload delivery system such as system 100. In some embodiments, the microfluidic chips or filters (or any other element comprising one or more constrictions configured to perturb the membranes of the cells) may be provided and fluidly connected to a system such as system 100 by way of a constriction cartridge. A constriction cartridge may be any device configured to house an element comprising a constriction, such as a microfluidic chip or a filter, and/or to facilitate the fluid connection of the element (e.g., chip or filter) to another portion of an intracellular payload delivery system, such as system 100.

As shown in FIG. 1, system 100 may comprise base plate 102, housing 103, hook 104, input bag 106, preparation vessel housing 110, output bag tray area 111, output bag 112, display 120, and cartridge 124. In some embodiments, these elements may share any one or more characteristics in common with the corresponding elements described with respect to FIG. 15A and associated figures and description in PCT/US18/66295. In some embodiments, cell suspension fluid may be held in a preparation vessel of system 100 (e.g., housed inside preparation vessel housing 110, and may then be caused to flow (e.g., under pressure) out of the preparation vessel and through constriction cartridge 124. Inside constriction cartridge 124, the cell suspension fluid may be caused to flow through one or more elements (e.g., microfluidic chips or filters) having one or more constricting channels and/or pores. After flowing through the one or more elements inside constriction cartridge 124, the cell suspension fluid may then flow out of constriction cartridge 124, and may flow toward and into one or more downstream system components, including output bag 112.

Below, exemplary embodiments of improved constriction cartridges for use in systems for intracellular payload delivery, such as constriction cartridge 112 for use in system 100, are described.

Figure 2A:
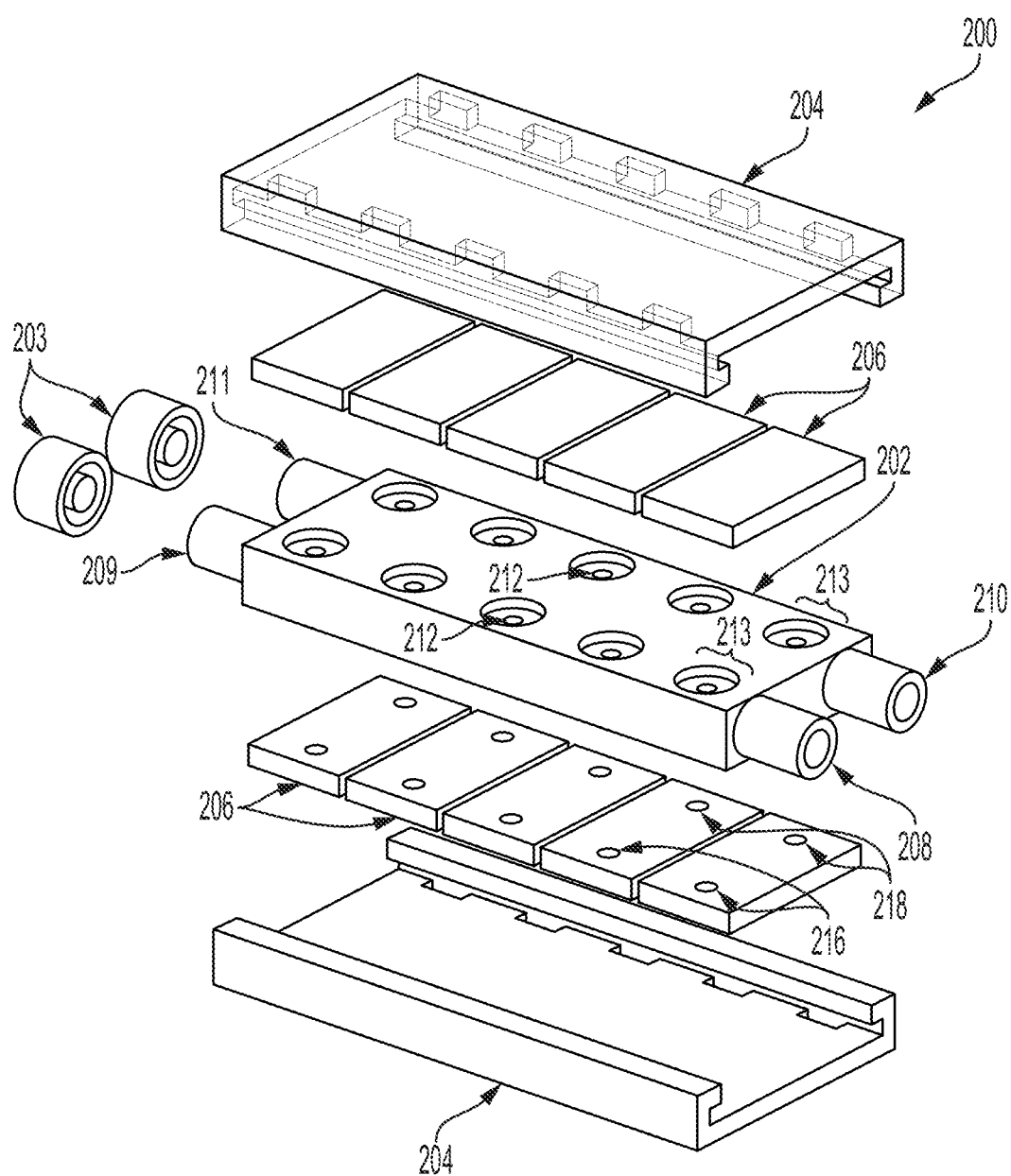
FIGS. 2A-2C illustrate various views of a constriction cartridge for use in a tabletop system for delivering a payload to a cell, in accordance with some embodiments.
Figure 2B:
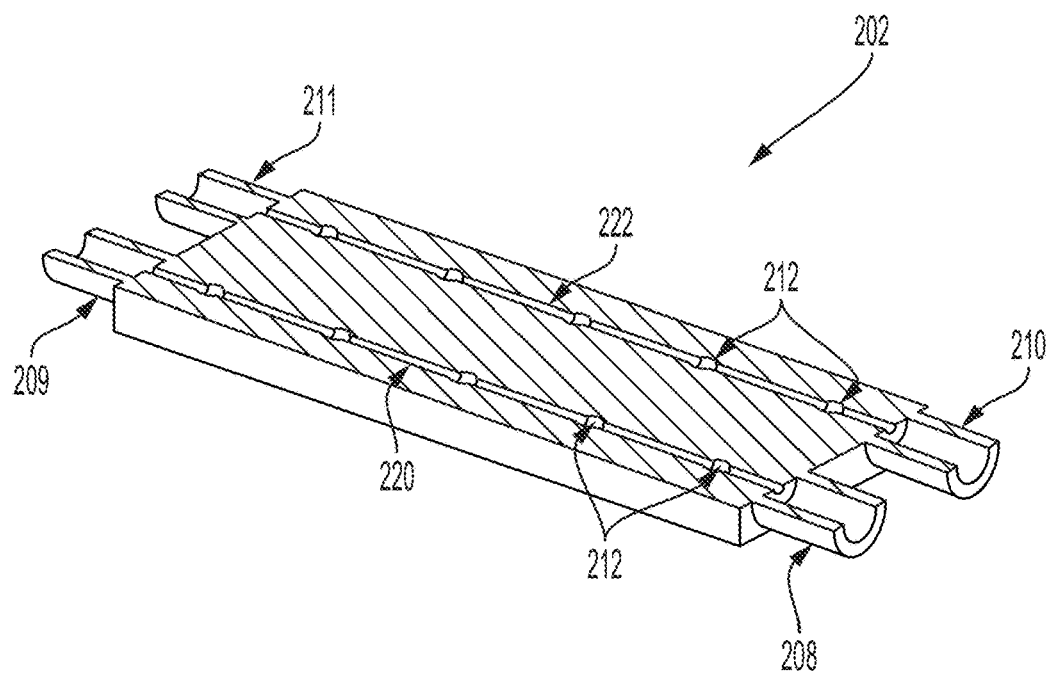
Figure 2C:
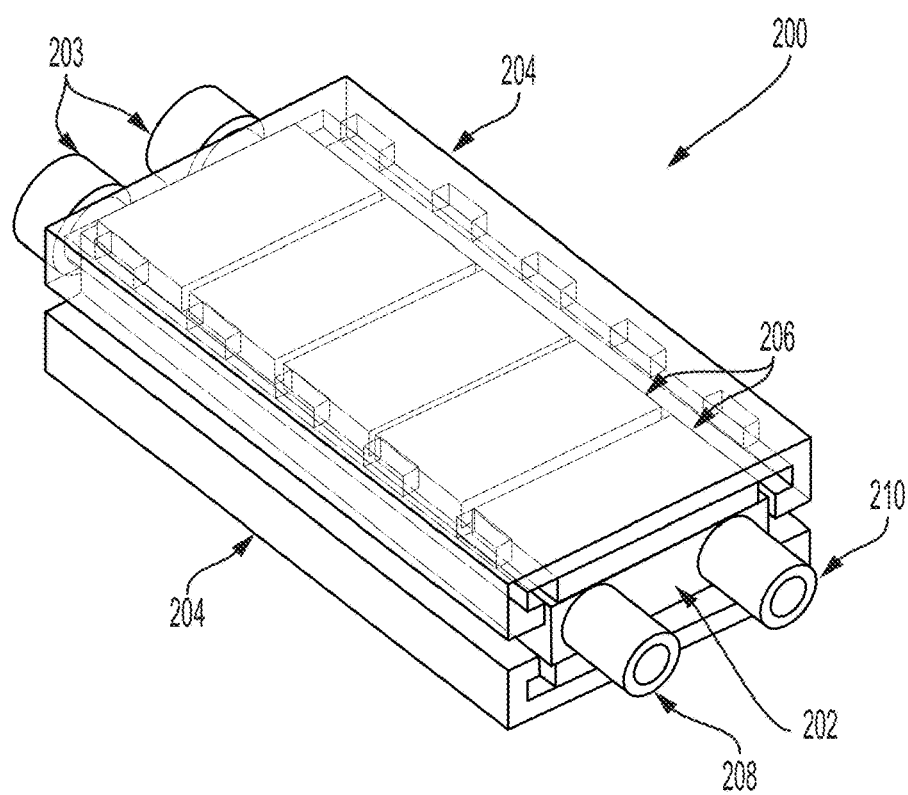

FIGS. 2A-2C illustrate various views of a constriction cartridge 200 for use in a tabletop system for delivering a payload to a cell, in accordance with some embodiments. In some embodiments, constriction cartridge 200 is the same constriction cartridge 124 as discussed above with reference to FIG. 1. FIG. 2A illustrates an exploded view of the constriction cartridge, in accordance with some embodiments; FIG. 2B illustrates a cross-sectional view of a body of the constriction cartridge, in accordance with some embodiments; and FIG. 2C illustrates a partially transparent view of the constriction cartridge, in accordance with some embodiments.

In some embodiments, constriction cartridge 200 may be any structure configured to contain or to house one or more constriction-containing elements, such as a constricting filter (containing one or more constricting pores) or a constricting microfluidic chip (containing one or more constricting microfluidic channels). (Constricting filters in accordance with some embodiments are disclosed in application number WO/2017/041050A1, which is hereby incorporated by reference in its entirety.) It should be noted that, in some embodiments, a constricting microfluidic channel or a constricting pore may simply be referred to as a "constriction" or a "cell-deforming constriction." A constriction-containing element may be any component, device, part, or the like having a channel, passage, or other opening (e.g., a constriction) having a smaller diameter than a cell of a cell suspension passing through the element, such that forcing the cell through the opening under pressure causes a perturbation in the membrane of the cell as the cell is constricted by the opening. In some embodiments, constriction cartridge 200 may include integrated constricting filters or microfluidic channels configured to constrict cells, while in some embodiments constriction cartridge 200 may be configured to house distinct elements (e.g., chips or filters) that themselves include constricting pores or constricting microfluidic channels. In either case, constriction cartridge 200 may define part of the flow path of a system for delivering a payload to a cell, such as system 100, such that a cell suspension may flow from a preparation vessel of the system toward and into constriction cartridge 200, and such that the cell suspension may then flow through and out of constriction cartridge 200 and toward and into an output bag of the system (or any other suitable downstream flow path components).

As shown, constriction cartridge 200 may comprise body 202, caps 203, removable covers 204, inlet 208, outlet 210, ports 209 and 211, branch channels 212, o-ring cavities 213, input channel 220, and output channel 222. Constriction cartridge 200 may be configured to cause cell suspension (and/or buffer fluid or other fluid) to flow into and through constriction-containing elements 206, which may be constricting microfluidic chips having a plurality of constricting microfluidic channels and/or constricting filters having a plurality of constricting openings or pores. In either event, constriction-containing elements 206 may have respective constriction-containing element inlets 216 for fluid to flow into the respective elements and respective constriction cartridge outlets 218 for fluid to flow out of the respective elements. Constriction cartridge 200 may be configured to receive one or more constriction-containing elements 206 and to hold them in place using one or more grooves or ridges, and/or by using friction force applied by one or more deformable components such as o-rings when removable covers 204 are in place on cartridge 200.

In the example of FIGS. 2A-2C, constriction cartridge 200 comprises constriction cartridge inlet 208 and constriction cartridge outlet 210 disposed on cartridge body 202 and defining a beginning and end of the flow path for cell suspension and/or buffer fluid flowing through constriction cartridge 200. In some embodiments, inlet 208 and outlet 210 may include any one or more connection mechanisms suitable for creating and securing a fluid connection between the inlet or outlet and another fluid-carrying component of a system in which cartridge 200 is used; for example, a connection mechanism may include a threaded connection mechanism and/or a Luer-type connection mechanism.

As shown, inlet 208 and outlet 210 may be disposed on a same side and/or a same face of body 202. In some embodiments, inlet 208 and/or outlet 210 may be define tube-shaped protrusions from body 202 that extend in a direction outward and away from the center of body 202. In some embodiments, inlet 208 and outlet 210 may be interchangeable with one another, depending on user preference; that is, cartridge 200 may be reversible with respect to function and/or orientation of inlet 208 and outlet 210.

Alternately or in addition to being optionally reversible with respect to inlet 208 and outlet 210, cartridge 200 may, in some embodiments, be optionally reversible as to the pair of ports 209 and 211 and the pair of inlets/outlets 208 and 210. As shown in FIGS. 2A-2C, ports 209 and 211 may extend from body 202 in a direction outward and away from the center of body 202 and opposite the direction in which inlet/outlet 208 and 210 extending in the direction opposite that of inlet 208 and outlet 210. In some embodiments, body 202 may be symmetrical along three different axes, all perpendicular to one another, such that each end of body 202 has two ports, one on each side of a center line of body 202. Manufacturing of body 202, for example by molding, may be made more efficient by making the body symmetrical in this manner, even when that means that the body will have four ports, and even if only two ports are to be used in the application of body 202.

As shown in FIG. 2B, ports 209 and 211 may be blocked by caps 203, which may attach to the ports by adhesive, threaded connection, Luer lock connector, or the like. By capping ports 209 and 211, a flow path may be defined between the two other ports: inlet 208 and outlet 210. In some other embodiments, other ports could be capped to define different flow paths through body 202 (e.g., capping inlet 208 and outlet 210 to define a flow path between port 209 and port 211; capping inlet 208 and port 211 to define a flow path between outlet 210 and port 209; or capping outlet 210 and port 209 to define a flow path between inlet 208 and port 211). By capping two of the four ports on body 202, a flow path beginning at a single port and ending at a single port may thus be created. In some alternate embodiments, body 202 may be constructed with only two ports, such that a flow path may be defined between the two ports without needing to cap or otherwise block any other ports, and channels 220 and 222 (explained in further detail below) may terminate before an end of body 202 opposite inlet 208 and outlet 210. While different configurations are possible as discussed above, this description will proceed with respect to the exemplary arrangement shown in FIGS. 2A-2C, in which ports 209 and 211 are blocked by caps 203, thereby defining a flow path from inlet 208 to outlet 210.

As stated above, a flow path through cartridge 200 may be defined beginning at inlet 208 and ending at outlet 210. Between inlet 208 and outlet 210, the flow path through cartridge 200 may pass through one or more constriction-containing elements (e.g., microfluidic chips or filters), such that fluid flowing into inlet 208 must flow through one or more constriction-containing elements before the fluid flows out of outlet 210. In some embodiments, a plurality of constriction-containing elements in cartridge 200 may be arranged in series, such that the flow path through cartridge 200 may be a single linear path. In some embodiments, a plurality of constriction-containing elements in cartridge 200 may be arranged in parallel, such that the flow path in cartridge 200 diverges into a plurality of parallel segments as fluid travels through constriction cartridge 200, and may then re-converge before flowing out of constriction cartridge 200. In some embodiments, three or more constriction-containing elements may be arranged in cartridge 200 such that one or more of the elements are in series with another of the constriction-containing elements and one or more of the elements are in parallel with another of the constriction-containing elements.

As shown in FIG. 2B, body 202 may comprise channels input channel 220 and output channel 222, each defined through an interior volume of body 202. Input channel 220 and output channel 222 may each be fluidly connected to a plurality of branch channels 212 that are defined through an interior volume of body 202 and join to and/or intersect with the channels, for example at a perpendicular angle. In the example shown in FIG. 2B, branch channels 212 extend from a top side of body 202 through to a bottom side of body 202, intersecting the input and output channels at the center of the body. Branch channels 212 may, in some embodiments, allow flow of fluid between the input and output channels and constriction-containing elements 206. In some embodiments, branch channels 212 may be positioned in a manner such that they will align with constriction-containing element inlets 216 and/or constriction-containing element outlets 218 when constriction-containing elements 206 are placed in cartridge 200. It should be noted that branch channels 212 may in some embodiments extend only in a single direction from an input channel or output channel, or in some embodiments may extend in multiple different directions from an input channel or output channel. In the example shown in FIGS. 2A-2C, branch channels 212 may extend in opposite directions upward and downward through body 202, away from the input and output channels in opposite directions, such that fluid may flow to/from the input and output channels from/to different constriction-containing elements that may be placed on opposite sides (e.g., top and bottom) of body 202.

Branch channels 212 may also be aligned along a shared axis with a respective one of cavities 213 (or a respective pair of cavities 213, one on the top side of body 202 and one on the bottom side of body 202), each of which may be formed as a recessed cavity on a surface of body 202. Cavities 213 may be configured to receive an o-ring, such that the o-ring may sit inside a cavity 213 between body 202 and one of constriction-containing elements 206, allowing a fluid-tight seal to be formed between body 202 and the constriction-containing elements, such that fluid may flow through the cavity and through the center of the o-ring, thereby flowing between the body and the constriction-containing element without leaking out from the flow path defined in part by the o-ring. In some embodiments, other sealing options aside from or in addition to o-rings may be used to create a seal for a fluid connection between a constriction cartridge and a constriction-containing element; for example, over-molding, chemical bonding, and/or mechanical interlocks may be used.

Thus, in some embodiments, fluid may enter cartridge 200 through inlet 208, flow from inlet 208 into and through input channel 220, flow from input channel 220 into and through one of the branch channels 212 that intersects input channel 220, flow from one of the branch channels 212 into and through one of the cavities 213 aligned with the branch channel, flow from one of the cavities 213 into one of constriction-containing element inlets 216, flow from the constriction-containing element inlet 216 through the constriction-containing element 206, flow out of the constriction-containing element 206 through its constriction-containing element outlet 218, flow from the constriction-containing element outlet 218 into and through another one of the cavities 213 aligned with a branch channel 212 that intersects output channel 222, flow from that second one of the cavities 213 into and through an aligned one of the branch channels 212, flow from that second one of the branch channels 212 into and through output channel 222, and flow from output channel 222 to and through outlet 210 to exit cartridge 200. Thus, in short, fluid such as buffer fluid or cell suspension may flow into constriction cartridge 200 and may be passed through one or more constriction-containing elements before flowing out of constriction cartridge 200.

In some embodiments, constriction cartridge 200 may be configured to be able to receive a blank placeholder element in place of a functional constriction-containing element, wherein the blank placeholder element may not contain any channels or pores, or may otherwise be configured to disallow flow through the portion of constriction cartridge 200 housing the placeholder element. By using a blank placeholder element, constriction cartridge 200 may cause flow of fluid through a smaller number of constriction-containing elements at a time, or through only one constriction-containing element at a time, such that the system need not be used at the maximum capacity of constriction-containing elements at all times.

As shown in FIGS. 2A-2C, constriction cartridge 200 may include removable covers 204, which may be elements configured to be placed alongside one or more constriction-containing elements 206, to press the one or more constriction-containing elements 206 toward cartridge body 202, and/or to otherwise hold the one or more constriction-containing elements 206 in place. In some embodiments, removable covers 204 may be configured to apply inward force to constriction-containing elements 206 to press them toward cartridge body 202 by way of one or more springs or other compressible or deformable components, such as rubber o-rings as discussed elsewhere herein. In some embodiments, removable covers 204 may be configured to press flush against a surface of one or more of constriction-containing elements 206. In some embodiments, removable cover 204 may serve to ensure that constriction-containing elements 206 do not delaminate a layer under the pressure of fluid being forced through them; by pressing a cover 204 against one face of a constriction-containing element 206 under force, the constriction-containing element 206 may be prevented from delaminating.

In some embodiments, one or more of removable covers 204 may be attached to one or more other components of cartridge 200 by a sliding connection, a threaded connection, a hinged connection, a tab-and-slot connection, a locking mechanism, by one or more screws, by one or more cams, or in any other suitable manner such that the cover may be removed, for example, to replace constriction-containing elements 206.

In some embodiments, a sliding connection, such as the connection shown in FIGS. 2A-2C, may allow cover 204 to slide laterally along cartridge 202 (in the direction of flow in and out of the cartridge shown in FIGS. 2A-2C), such that a lip of a cover 204 may slide onto a corresponding lip, protrusion, groove, or tooth of body 204. In some embodiments, a removable cover configured to slide onto and off of a body of a constriction cartridge may be configured to fully encircle a constriction cartridge body, in some embodiments thereby avoiding the need for interlocking grooves or teeth or the like.

A sliding connection such as this may be removed with minimal lateral force (e.g., force in the direction of sliding), but may provide great strength in the direction perpendicular to the sliding direction and extending away from the side of body 202 against which one or more constriction-containing elements 206 are placed. Thus, while the cover having a sliding connection may be easily removed by hand, it may nonetheless offer superior durability under pressure to other connection mechanisms that may be used to hand-assemble constriction cartridges, such attaching a cover by threaded components. In some embodiments, in addition to or alternately to one or more removable covers, a constriction cartridge may be configured to securely house one or more constriction-containing elements without use of removable covers.

In some embodiments, cartridge 200 may be less than or equal to 25 mm, 50 mm, 75 mm, 100 mm, 125 mm, 150 mm, or 200 mm in length (e.g., in the direction running parallel to channels 220 and 222). In some embodiments, cartridge 200 may be greater than or equal to 25 mm, 50 mm, 75 mm, 100 mm, 125 mm, 150 mm, or 200 mm in length.

In some embodiments, cartridge 200 may be less than or equal to 10 mm, 20 mm, 30 mm, 40 mm, 50 mm, or 60 mm in width (e.g., in the direction running perpendicular to and between channels 220 and 222). In some embodiments, cartridge 200 may be greater than or equal to 10 mm, 20 mm, 30 mm, 40 mm, 50 mm, or 60 mm in width.

In some embodiments, cartridge 200 may be less than or equal to 5 mm, 10 mm, 15 mm, 20 mm, 25 mm, or 30 mm in height (e.g., in the direction running from one cover 204 to the other). In some embodiments, cartridge 200 may be greater than or equal to 5 mm, 10 mm, 15 mm, 20 mm, 25 mm, or 30 mm in height.

In some embodiments, one or more of constriction-containing elements 206 may be less than or equal to 20 mm, 30 mm, 40 mm, 50 mm, or 60 mm in length (e.g., in the direction running from inlet 216 toward outlet 218). In some embodiments, one or more of constriction-containing elements 206 may be greater than or equal to 20 mm, 30 mm, 40 mm, 50 mm, or 60 mm in length.

In some embodiments, one or more of constriction-containing elements 206 may be less than or equal to 20 mm, 30 mm, 40 mm, 50 mm, or 60 mm in width (e.g., in the direction perpendicular to channels 220 and 222 in the arrangement shown in FIG. 2A). In some embodiments, one or more of constriction-containing elements 206 may be greater than or equal to 20 mm, 30 mm, 40 mm, 50 mm, or 60 mm in width.

In some embodiments, one or more of constriction-containing elements 206 may be less than or equal to 0.1 mm, 0.5 mm, 1 mm, 2 mm, 3 mm, or 5 mm in thickness (e.g., in the direction running from one cover 204 to the other in the arrangement shown in FIG. 2A). In some embodiments, one or more of constriction-containing elements 206 may be greater than or equal to 0.1 mm, 0.5 mm, 1 mm, 2 mm, 3 mm, or 5 mm in thickness.

In some embodiments, a constriction (e.g., a constricting channel or constricting pore) of a constriction-containing element (e.g., one of elements 206) may be less than or equal to 0.25 µm, 0.5 µm, 1 µm, 5 µm, 10 µm, 20 µm, or 50 µm in width. In some embodiments, a constriction (e.g., a constricting channel or constricting pore) of a constriction-containing element (e.g., one of elements 206) may be greater than or equal to 0.25 µm, 0.5 µm, 1 µm, 5 µm, 10 µm, 20 µm, or 50 µm in width.

In some embodiments, a constriction (e.g., a constricting channel or constricting pore) of a constriction-containing element (e.g., one of elements 206) may be less than or equal to 1 µm, 5 µm, 10 µm, 20 µm, 30 µm, 40 µm, 50 µm, or 100 µm in length. In some embodiments, a constriction (e.g., a constricting channel or constricting pore) of a constriction-containing element (e.g., one of elements 206) may be greater than or equal to 1 µm, 5 µm, 10 µm, 20 µm, 30 µm, 40 µm, 50 µm, or 100 µm in length.

In some embodiments, a constriction (e.g., a constricting channel or constricting pore) of a constriction-containing element (e.g., one of elements 206) may be less than or equal to 10 µm, 15 µm, 20 µm, 50 µm, 80 µm, 100 µm, or 200 µm in depth. In some embodiments, a constriction (e.g., a constricting channel or constricting pore) of a constriction-containing element (e.g., one of elements 206) may be greater than or equal to 10 µm, 15 µm, 20 µm, 50 µm, 80 µm, 100 µm, or 200 µm in depth.

In some embodiments, one or more of input channel 220 and output channel 222 may be less than or equal to 25 mm, 50 mm, 75 mm, 100 mm, 125 mm, 150 mm, or 200 mm in length. In some embodiments, one or more of input channel 220 and output channel 222 may be greater than or equal to 25 mm, 50 mm, 75 mm, 100 mm, 125 mm, 150 mm, or 200 mm in length.

In some embodiments, one or more of input channel 220 and output channel 222 may be less than or equal to 2 mm, 3 mm, 3.25 mm, 3.5 mm, 3.75 mm, 4 mm, or 5 mm in diameter. In some embodiments, one or more of input channel 220 and output channel 222 may be greater than or equal to 2 mm, 3 mm, 3.25 mm, 3.5 mm, 3.75 mm, 4 mm, or 5 mm in diameter. In some embodiments, one or more of input channel 220 and output channel 222 may have a diameter such that the diameter may match or essentially match the diameter of a channel or opening to which the input or output channel is configured to connect; for example, one or more of input channel 220 and output channel 222 may have a diameter of about 3.7 mm to match a standard Leur feature to which the input and output channels are configured to connect.

In some embodiments, one or more of branch channels 212 may be less than or equal to 5 mm, 10 mm, 15 mm, 20 mm, 25 mm, or 30 mm in length. In some embodiments, one or more of input channel 220 and output channel 222 may be greater than or equal to 5 mm, 10 mm, 15 mm, 20 mm, 25 mm, or 30 mm in length.

In some embodiments, one or more of branch channels 212 may be less than or equal to 2 mm, 3 mm, 3.25 mm, 3.5 mm, 3.75 mm, 4 mm, or 5 mm in diameter. In some embodiments, one or more of input channel 220 and output channel 222 may be greater than or equal to 2 mm, 3 mm, 3.25 mm, 3.5 mm, 3.75 mm, 4 mm, or 5 mm in diameter. In some embodiments, a diameter of one or more of branch channels 212 may be equal to a diameter of input channel 220 and/or output channel 222. In some embodiments, a diameter of one or more of branch channels 212 may be less than a diameter of input channel 220 and/or output channel 222. In some embodiments, a diameter of one or more of branch channels 212 may be greater than a diameter of input channel 220 and/or output channel 222. In some embodiments, the combined cross-sectional area of all branch channels 212 in a single constriction-containing element 206 may be equal to a cross-sectional area of input channel 220. In some embodiments, the combined cross-sectional area of all branch channels 212 in a single constriction-containing element 206 may be equal to a cross-sectional area of output channel 222.

In some embodiments, cartridge 200 may be configured to be able to be used with systems that force fluid through the cartridges at pressures of less than or equal to 1, 5, 10, 25, 50, 75, 100, 125, 150, or 200 PSI. In some embodiments, cartridge 200 may be configured to be able to be used with systems that force fluid through the cartridges at pressures of greater than or equal to 1, 5, 10, 25, 50, 75, 100, 125, 150, or 200 PSI. In some embodiments, cartridge 200 may be configured to be used with constriction-containing elements (e.g., constriction-containing elements) that may each individually (e.g., on a "per chip" basis) provide a throughput of less than or equal to 50, 100, 150, 200, 250, 300, or 400 mL of red-blood-cell suspension per minute. In some embodiments, cartridge 200 may be configured to be used with constriction-containing elements (e.g., constriction-containing elements) that may each individually (e.g., on a "per chip" basis) provide a throughput of greater than or equal to 50, 100, 150, 200, 250, 300, or 400 mL of red-blood-cell suspension per minute.

In some embodiments, cartridge 200 may be configured to be used with constriction-containing elements (e.g., constriction-containing elements) that may each individually (e.g., on a "per chip" basis) provide a throughput of less than or equal to 25, 50, 75, 100, 125, 150, or 200 mL of peripheral-blood-mononuclear-cell suspension per minute.

In some embodiments, cartridge 200 may be configured to be used with constriction-containing elements (e.g., constriction-containing elements) that may each individually (e.g., on a "per chip" basis) provide a throughput of greater than or equal to 25, 50, 75, 100, 125, 150, or 200 mL of peripheral-blood-mononuclear-cell cell suspension per minute.

In some embodiments, cartridge 200 may have an overall fluid throughput (e.g., including all constriction-containing elements housed in in cartridge 200) of less than or equal to 0.25, 0.5, 1, 1.5, 2, 2.5, or 5 L/min. In some embodiments, cartridge 200 may have an overall fluid throughput (e.g., including all constriction-containing elements housed in in cartridge 200) of greater than or equal to 0.25, 0.5, 1, 1.5, 2, 2.5, or 5 L/min.

In some embodiments, cartridge 200 may be configured to house a plurality off constriction-containing elements, such as constriction-containing elements 206. In some embodiments, cartridge 206 may be configured to house fewer than or equal to 2, 5, 10, or 20 constriction-containing elements. In some embodiments, cartridge 206 may be configured to house fewer than or equal to 2, 5, 10, or 20 constriction-containing elements per side. In some embodiments, cartridge 206 may be configured to house greater than or equal to 2, 5, 10, or 20 constriction-containing elements. In some embodiments, cartridge 206 may be configured to house greater than or equal to 2, 5, 10, or 20 constriction-containing elements per side.

In some embodiments, cartridge 200 may comprise one or more components made of metal, plastic, polymers, and/or glass. In some embodiments cartridge 200 may comprise one or more components made of polycarbonate, polypropylene, and/or polymethyl methacrylate.

Figure 3A:
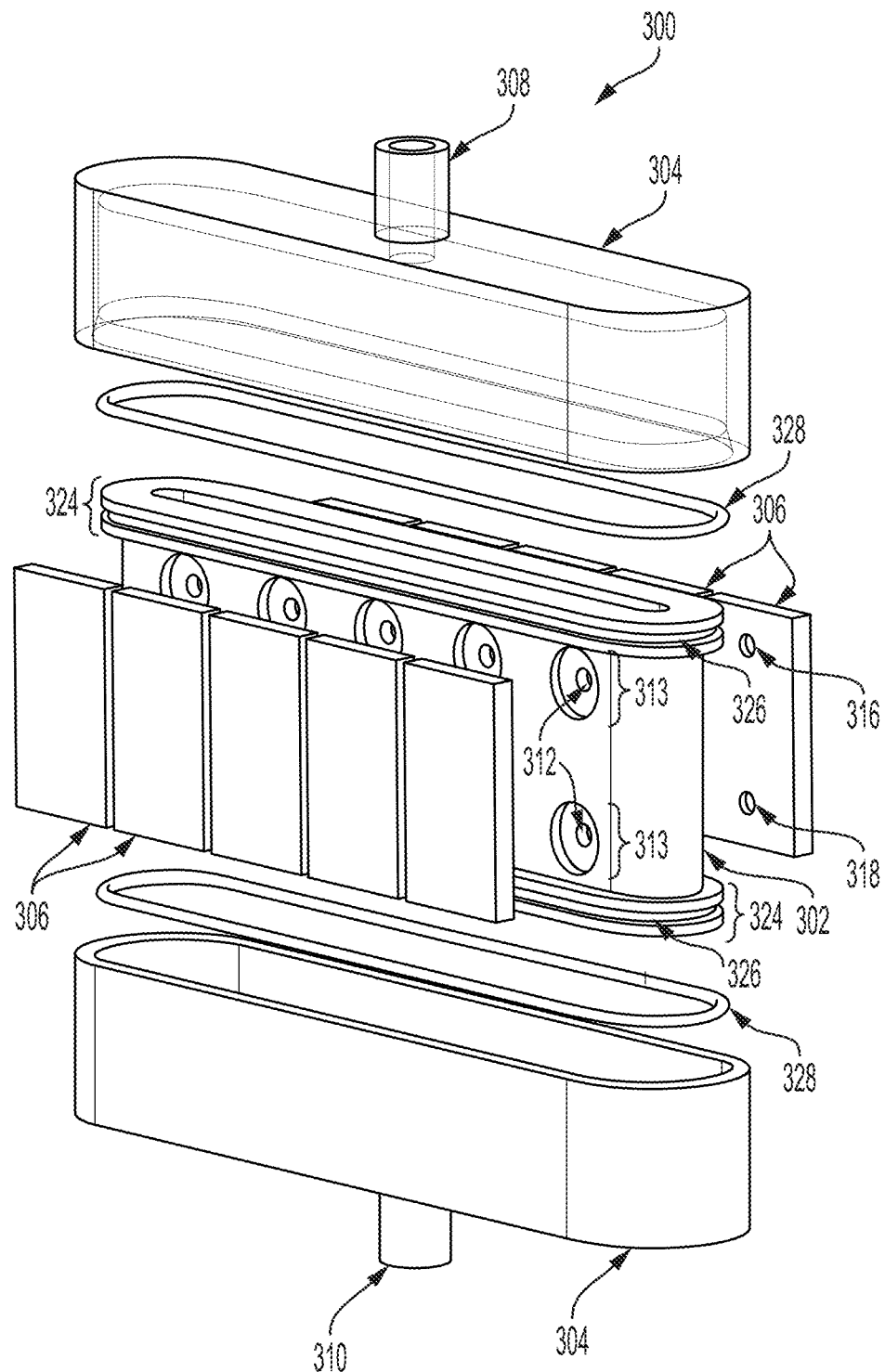
FIGS. 3A-3C illustrate various views of a constriction cartridge for use in a tabletop system for delivering a payload to a cell, in accordance with some embodiments.
Figure 3B:
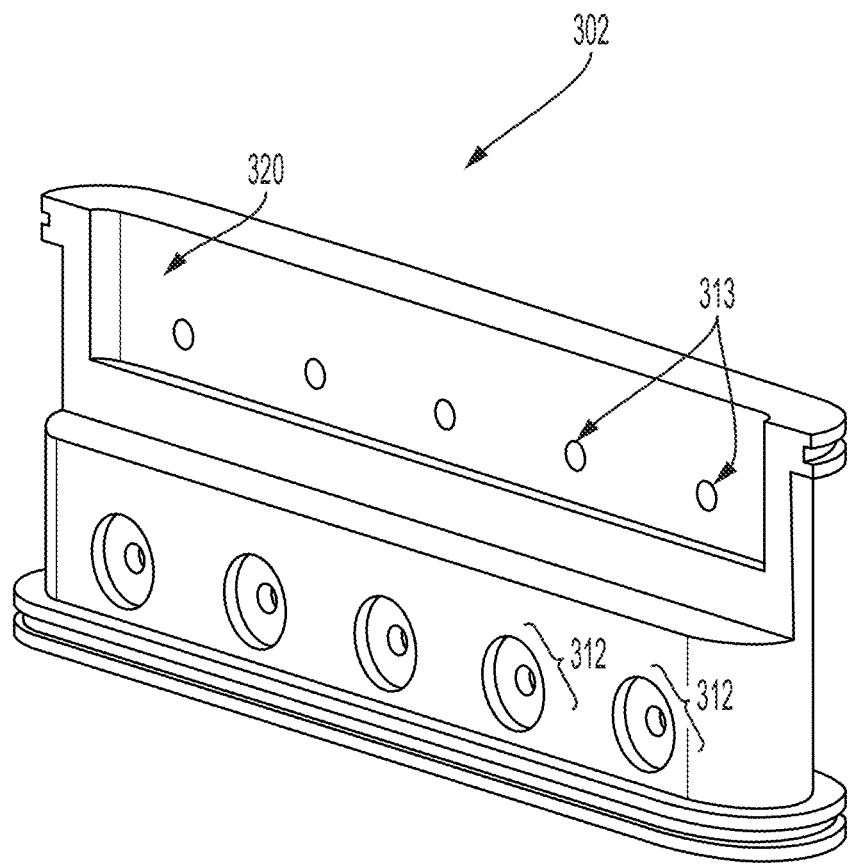
Figure 3C:
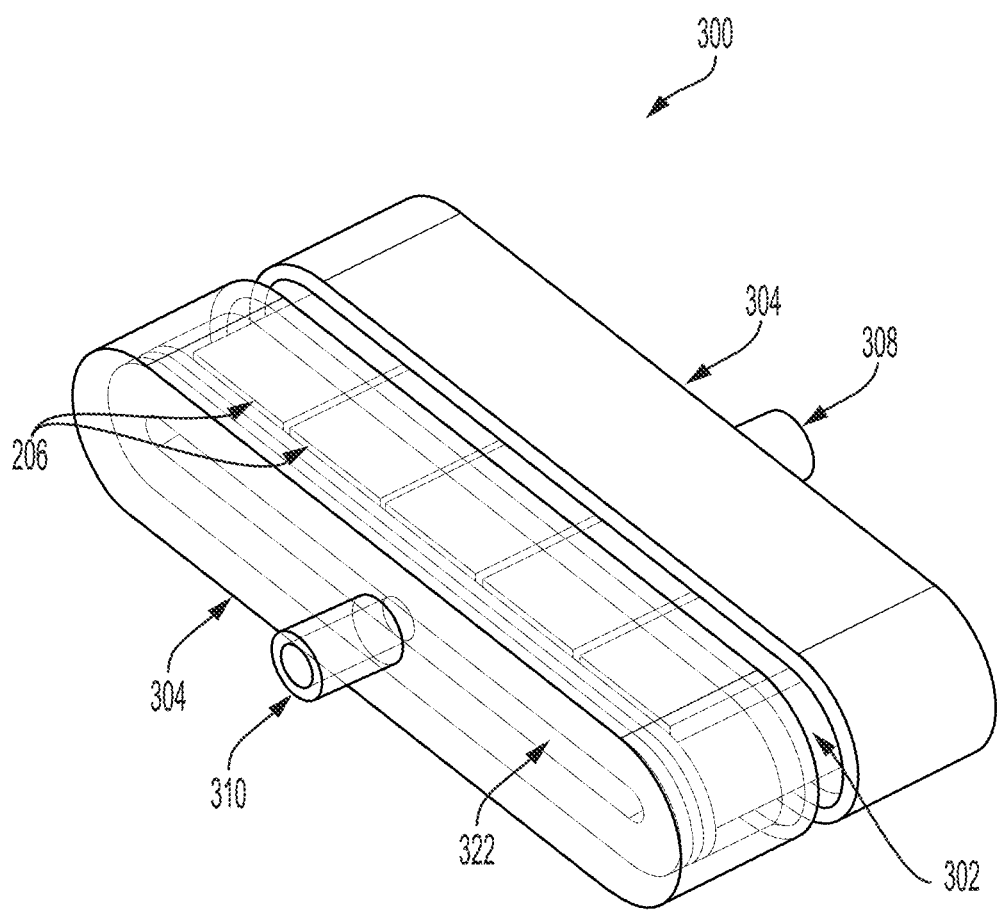

FIGS. 3A-3C illustrate various views of a constriction cartridge 300 for use in a tabletop system for delivering a payload to a cell, in accordance with some embodiments. In some embodiments, constriction cartridge 300 is the same constriction cartridge 124 as discussed above with reference to FIG. 1. FIG. 3A illustrates an exploded view of the constriction cartridge, in accordance with some embodiments; FIG. 3B illustrates a partial cross-sectional view of a body of the constriction cartridge, in accordance with some embodiments; and FIG. 3C illustrates a partially transparent view of the constriction cartridge, in accordance with some embodiments.

In some embodiments, cartridge 300 may share any one or more characteristics in common with cartridge 200. In some embodiments, one or more components of cartridge 300 may share any one or more characteristics in common with a corresponding component or components of cartridge 200. In some embodiments, as discussed below, cartridge 300 may differ from cartridge 200 in that, while cartridge 200 may comprise inlet and outlet ports formed as part of the cartridge body and fluidly connected to internal channels formed in the cartridge body, cartridge 300 may instead comprise inlet and outlet ports that are formed as a part of removable caps of the cartridge (rather than the body) and that are configured to be fluidly connected to internal chambers formed in the cartridge body when the caps are positioned on the cartridge body in the assembled position. Thus, while the fluid path in cartridge 200 may be defined by a single cartridge component (e.g., the cartridge body) in conjunction with one or more constriction-containing elements, the fluid path in cartridge 300 may be defined by three separate cartridge components (e.g., the cartridge body and two removable covers) in conjunction with one or more constriction-containing elements.

As shown, constriction cartridge 300 may comprise body 302, removable covers 304, inlet 308, outlet 310, branch channels 312, o-ring cavities 313, input chamber 320, output chamber 222, raised lip 324, groove 326, and body o-rings 328. Constriction cartridge 300 may be configured to cause cell suspension (and/or buffer fluid or other fluid) to flow into and through constriction-containing elements 306, which may be constricting microfluidic chips having a plurality of constricting microfluidic channels and/or constricting filters having a plurality of constricting openings or pores. In either event, constriction-containing elements 306 may have respective constriction-containing element inlets 316 for fluid to flow into the respective elements and respective constriction cartridge outlets 318 for fluid to flow out of the respective elements. Constriction cartridge 300 may be configured to receive one or more constriction-containing elements 306 and to hold them in place using one or more grooves or ridges, and/or by using friction force applied by one or more deformable components such as o-rings when removable covers 304 are in place on cartridge 300. In some embodiments, components of constriction cartridge 300 and/or of constriction-containing elements 306 may share any one or more characteristics in common with corresponding components discussed above with respect to FIGS. 2A-2C.

Body 302 of cartridge 300 may share any one or more characteristics in common with body 202 of cartridge 200, but instead of (or in additional to) internal input and output channels, body 302 may have an input chamber 320 (as shown in FIGS. 3A and 3B) and an output chamber 322 (as shown in FIG. 3C). Input chamber 320 and output chamber 322 may be chambers formed in an interior volume of body 302 and each opening to one side of body 302. The opening of a chamber to the outside of body 302 may be an elongated opening as shown in FIGS. 3A-3C. As shown in FIG. 3B, input chamber 320 may extend from its elongated opening on one side of body 302 toward the center of body 302, but may be separated from output chamber 322 by a wall portion or divider portion in body 302, such that the two chambers do not meet. In some embodiments, input chamber 320 and output chamber 322 may serve a similar purpose as input channel 220 and output channel 222 discussed above, in that they may guide the flow of fluid to and from branch channels 312.

In some embodiments, one or more of input chamber 320 and output chamber 322 may be less than or equal to 10 mm, 15 mm, 20 mm, 25 mm, 50 mm, 75 mm, 100 mm, 125 mm, 150 mm, or 195 mm in length (e.g., in the direction running in the elongated dimension of the opening formed in the side of cartridge 300, along the surface of the side of cartridge 300). In some embodiments, one or more of input chamber 320 and output chamber 322 may be greater than or equal to 10 mm, 15 mm, 20 mm, 25 mm, 50 mm, 75 mm, 100 mm, 125 mm, 150 mm, or 195 mm in length.

In some embodiments, one or more of input chamber 320 and output chamber 322 may be less than or equal to 1 mm, 2.5 mm, 5 mm, 10 mm, 15 mm, 20 mm, or 25 mm, in width (e.g., in the direction running perpendicular to the elongated dimension of the opening formed in the side of cartridge 300, along the surface of the side of cartridge 300). In some embodiments, one or more of input chamber 320 and output chamber 322 may be greater than or equal to 1 mm, 2.5 mm, 5 mm, 10 mm, 15 mm, 20 mm, or 25 mm, in width.

In some embodiments, one or more of input chamber 320 and output chamber 322 may be less than or equal to 2.5 mm, 5 mm, 10 mm, 15 mm, 20 mm, 25 mm, 30 mm, 40 mm, 50 mm, or 55 mm in depth (e.g., in the direction running from the opening on the side of cartridge 300 toward the interior of cartridge 300). In some embodiments, one or more of input chamber 320 and output chamber 322 may be greater than or equal to 2.5 mm, 5 mm, 10 mm, 15 mm, 20 mm, 25 mm, 30 mm, 40 mm, 50 mm, or 55 mm in depth.

Cartridge 320 may comprise removable covers 304, which may serve at least two functions. First, removable covers 304 may serve to hold constriction-containing elements 306 in place against body 302 when removable covers are slid over constriction-containing elements 306, in a similar manner as removable covers 204 discussed above. In some embodiments, removable covers 304 may be configured to press flush against a surface of one or more of constriction-containing elements 306. In some embodiments, removable cover 304 may serve to ensure that constriction-containing elements 306 do not delaminate a layer under the pressure of fluid being forced through them; by pressing a cover 304 against one face of a constriction-containing element 306 under force, the constriction-containing element 306 may be prevented from delaminating.

In some embodiments, one or more of removable covers 304 may be attached to one or more other components of cartridge 300 by a sliding connection, a threaded connection, a hinged connection, a tab-and-slot connection, a locking mechanism, by one or more screws, by one or more cams, or in any other suitable manner such that the cover may be removed, for example, to replace constriction-containing elements 306. In some embodiments, removable cover 304 may be shaped so as to fit tightly around body 302, for example by sliding onto and over all or part of body 302.

In some embodiments, a sliding connection, such as the connection shown in FIGS. 3A-3C, may allow covers 304 to slide laterally along cartridge 302 (in the direction of flow in and out of the ports on sliding covers 304 shown in FIGS. 3A-3C). As shown in FIGS. 3A and 3C, removable covers 304 may be shaped so as to have an open side opposite an inlet/outlet, such that the open side may slide over a portion of body 302 in order to secure elements 306 in place and to form a fluid connection with an input chamber or output chamber in body 302 that opens toward the cover.

A sliding connection such as this may be removed with minimal lateral force (e.g., force in the direction of sliding), but may provide great strength in the direction perpendicular to the sliding direction and extending away from the side of body 302 against which one or more constriction-containing elements 306 are placed. Thus, while the cover having a sliding connection may be easily removed by hand, it may nonetheless offer superior durability under pressure to other connection mechanisms that may be used to hand-assemble constriction cartridges, such attaching a cover by threaded components. In some embodiments, in addition to or alternately to one or more removable covers, a constriction cartridge may be configured to securely house one or more constriction-containing elements without use of removable covers.

Second, removable covers 304 may serve to fluidly connect the input/output chambers in body 302 to other components of a system for delivering a payload to a cell, by way of inlet 308 and outlet 310, each of which may be comprised respectively in one of the removable covers 304. As shown, inlet 308 and outlet 310 may extend in opposite directions from one another when covers 304 are placed on cartridge 300, each extending in a direction perpendicular to the side of body 302 from which they extend, and in a direction aligned with the direction along which inlet 320 and outlets 322 extend into body 302. In some embodiments, inlet 308 and outlet 310 may include any one or more connection mechanisms suitable for creating and securing a fluid connection between the inlet or outlet and another fluid-carrying component of a system in which cartridge 200 is used; for example, a connection mechanism may include a threaded connection mechanism and/or a Luer-type connection mechanism.

In some embodiments, inlet 308 and outlet 310 may be interchangeable with one another, depending on user preference; that is, cartridge 300 may be reversible with respect to function and/or orientation of inlet 308 and outlet 310. In some embodiments, a cover 304 may be configured to fit onto either side of body 302, or onto only one side of body 302.

When removable covers 304 are slid into place on body 302, a fluid connection between a removable cover and the chamber in the body may be formed. Thus, whereas inlet 208 and outlet 210 in cartridge 200 were included as part of the cartridge body 202, inlet 308 and outlet 310 may be included as part of removable covers 304, such that fluid may enter cartridge 300 through a flow path in one of the removable covers 304, then flow into body 302, and then thereafter exit cartridge 300 through a flow path in the other one of the removable covers 304.

A fluid connection between a removable cover and a chamber in the body may, in some embodiments, be sealed in some embodiments by a body o-ring 328, which may sit in groove 326 formed in raised lip 324 formed on and/or around one or more edges of body 302. As shown, a raised lip 324 and a groove 326 may hold a body o-ring 328 in place and force body o-ring 328 against an inside surface of a removable cap 304, such that when the removable cap 304 is slid onto body 302 a seal is formed and fluid in the flow path inside removable cap 304 may flow into a chamber inside body 302 without leaking or otherwise escaping.

In addition to securing body o-ring 328 in place against an inside surface of a removable cap 304, a raised lip 326 may additionally serve to hold one or more of constriction-containing elements 306 in place. In some embodiments, the two raised lips 326 may be spaced apart from one another, for example along opposite edges of a surface of body 302, such that constriction-containing elements 306 may be placed in the recess formed between the raised lips 326, such that the constriction-containing elements 306 are prevented from sliding or moving laterally about and are properly aligned with branch channels 312 (e.g., branch channels 312 are aligned with respective constriction-containing element inlets 316 and constriction-containing element outlets 318).

As shown in FIG. 3A, constriction-containing elements 306 may comprise inlets 316 and outlets 318, which may share any one or more characteristics in common with the inlets 216 and outlets 218 described above with respect to FIGS. 2A-2C. Inlets 316 and outlets 318 may be configured to align with branch channels 312 and o-ring cavities 313, which may share any one or more characteristics in common with the branch channels 212 and o-ring cavities 213 described above with respect to FIGS. 2A-2C. For example, constriction-containing elements 306 may be pressed toward body 302 by removable covers 306, and may thereby be pressed into one or more o-rings housed in respective cavities 313, thereby forming a sealed flow path between constriction-containing elements 306 and the branch channels 312 aligned with the cavities 313 in body 302.

Branch channels 312 may, in some embodiments, differ from branch channels 212 as discussed above with reference to FIGS. 2A-2C in that branch channels 312 may intersect input chamber 320 or output chamber 322, rather than intersecting an input or output channel. In some embodiments, branch channels 312 may intersect an input or output chamber at a perpendicular angle to a surface of the chamber, as shown for example in FIG. 3B. In some embodiments, an axis of one of the branch channels 312 may be perpendicular both to an interior surface of an input/output chamber and to a direction along which the elongated opening of the input/output chamber runs along the surface of body 302.

It should be noted that branch channels 312 may in some embodiments extend only in a single direction from an input chamber or output chamber, or in some embodiments may extend in multiple different directions from an input chamber or output chamber. In the example shown in FIGS. 3A-3C, branch channels 312 may extend in opposite directions through body 302, away from the input and output chambers in opposite directions, such that fluid may flow to/from the input and output chambers from/to different constriction-containing elements that may be placed on opposite sides of body 302.

Thus, in some embodiments, fluid may enter cartridge 300 through inlet 308 of a removable cap 304, flow from inlet 308 into and through input chamber 320, flow from input chamber 320 into and through one of the branch channels 312 that intersects input chamber 320, flow from one of the branch channels 312 into and through one of the cavities 313 aligned with the branch channel, flow from one of the cavities 313 into one of constriction-containing element inlets 316, flow from the constriction-containing element inlet 316 through the constriction-containing element 306, flow out of the constriction-containing element 306 through its constriction-containing element outlet 318, flow from the constriction-containing element outlet 318 into and through another one of the cavities 313 aligned with a branch channel 312 that intersects output chamber 322, flow from that second one of the cavities 313 into and through an aligned one of the branch channels 312, flow from that second one of the branch channels 312 into and through output chamber 322, and flow from output chamber 322 to and through outlet 310 of the other removable cap 304 to exit cartridge 300. Thus, in short, fluid such as buffer fluid or cell suspension may flow into constriction cartridge 300 and may be passed through one or more constriction-containing elements before flowing out of constriction cartridge 300.

In some embodiments, constriction cartridge 300 may be configured to be able to receive a blank placeholder element in place of a functional constriction-containing element, wherein the blank placeholder element may not contain any channels or pores, or may otherwise be configured to disallow flow through the portion of constriction cartridge 300 housing the placeholder element. By using a blank placeholder element, constriction cartridge 300 may cause flow of fluid through a smaller number of constriction-containing elements at a time, or through only one constriction-containing element at a time, such that the system need not be used at the maximum capacity of constriction-containing elements at all times.

Example

Figure 4:
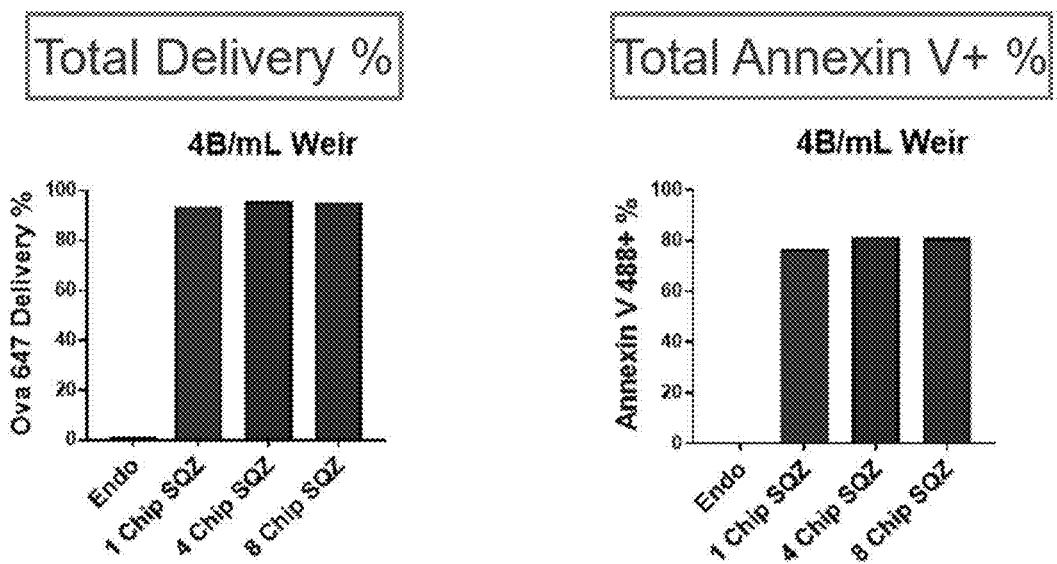
FIG. 4 shows data from a study evaluating how volumetric scaling is performed for passage of red blood cells through chips housed in a cartridge configured in accordance with cartridge characteristics disclosed herein.

FIG. 4 shows data from a study evaluating how volumetric scaling is performed for passage of red blood cells through chips housed in a cartridge configured in accordance with cartridge characteristics disclosed herein.

In the examples depicted, whole human blood was first leukoreduced before the constriction process, and was washed using a LOVO cell processing system. The blood was concentrated to ~4×10$^9$ red blood cells per mL. The prepared blood was then passed through one or more constriction-containing chips that were mounted in one of various different cartridges. The blood was passed through the respective cartridges at a pressure of 60 PSI along with 10 µg/mL ALEXA FLUOR 647 ovalbumin conjugate (a far-red fluorescent protein). Following passage of the blood through the respective cartridges, small-scale manual washing at 8000 RCF was performed. Cells in the blood were stained with ANNEXIN V ALEXA FLUOR 488 READY FLOW CONJUGATE. Flow cytometry was performed to assess ghost generation, ALEXA FLUOR 647 delivery percentage (to assess the percentage of cells for which delivery of the florescent protein was successful), delivery mean fluorescence intensity (MFI) (to assess the number of fluorescent proteins delivered to each cell, and ANNEXIN V ALEXA FLUOR 488+ percentage (to assess the percentage of cells to which the conjugate was successfully bonded to the cell membrane, which may be taken as indicative of cell age).

In various different runs performed, the same chips (SQZ Wier chips having a footprint of 11.5 mm by 21 mm) were used. In each cartridge configuration, the cartridge was tested to withstand up to 75 PSI. The number of chips used in the various cartridge configurations across different runs was one chip, four chips, or eight chips. For runs with one SQZ Weir chip, a clamshell-style cartridge was used; for runs with four SQZ Weir chips, a four-faced cartridge was used with one chip peer face; for runs with eight SQZ Weir chips, a double-sided cartridge holding four chips per side, configured in accordance with the embodiments shown in FIGS. 2A-2C above, was used. As shown in the graphs in FIG. 4, an endo control was also performed in which delivery and bonding percentage were measured for cells that were not passed through any constrictions.

As shown in the tables in FIG. 4, the use of the eight-chip configuration with the cartridge type depicted in FIGS. 2A-2C improved the volumetric flow rate (throughput in mL) and decreased the run time. As shown in the graphs in FIG. 4, there was little impact on performance for different cartridge configurations for total delivery percentage or for total ANNEXIN V ALEXA FLUOR 488+ percentage.

EMBODIMENTS

Below is an enumerated listing of certain embodiments. In some embodiments, any one or more of the features of any one or more of the embodiments below may be combined with any one or more of the other embodiments, even if the dependencies of the embodiments do not explicitly indicate that the embodiments may be combined.

1. A cartridge for delivering a payload to cells of a cell suspension, the cartridge comprising:
an input port configured to be fluidly connected to receive flow of the cell suspension;
a cartridge body comprising a first surface, the first surface configured to receive a first plurality of constriction-containing elements, each of the first plurality of constriction-containing elements comprising a respective constriction configured to perturb membranes of cells of the cell suspension to facilitate delivery of the payload to the cells;
an input channel formed in the cartridge body and configured to fluidly connect the input port to a first plurality of branch channels, wherein each of the first plurality of branch channels connects to the input channel and opens at a respective one of a first plurality of openings to the first surface of the cartridge body;

an output channel formed in the cartridge body, separate from the input channel, and configured to fluidly connect an output port to a second plurality of branch channels, wherein each of the second plurality of branch channels connects to the output channel and opens at a respective one of a second plurality of openings to the first surface of the cartridge body.

2. The cartridge of embodiment 1, wherein the first plurality of branch channels and the second plurality of branch channels are oriented in a direction perpendicular to the input channel and the output channel.

3. The cartridge of embodiment 2, wherein the first plurality of branch channels and the second plurality of branch channels are associated with one another in pairs of corresponding branch channels, such that fluid may flow from one branch channel of a pair through a constriction-containing element and into another branch channel of the same pair.

4. The cartridge of embodiment 3, wherein the branch channels of one or more of the pairs of corresponding branch channels are spaced apart from one another in a direction perpendicular to the input channel and the output channel and perpendicular to the direction of flow of fluid in the branch channels.

5. The cartridge of any one of embodiments 1-4, comprising a first removable cover configured to hold the first plurality of constriction-containing elements in place against the first surface of the cartridge body, wherein the first removable cover is removable to facilitate removal or replacement of the first plurality of constriction-containing elements.

6. The cartridge of embodiment 5, wherein the first removable cover is configured to attach to the cartridge body via a sliding connection, such that the first removable cover slides over the first plurality of constriction-containing elements as it is attached to the cartridge body.

7. The cartridge of embodiment 6, wherein the first removable cover is configured to slide in a direction parallel to the input channel and the output channel.

8. The cartridge of any one of embodiments 6-7, wherein the first removable cover is configured to slide in a direction perpendicular to the first plurality of branch channels and the second plurality of branch channels.

9. The cartridge of any one of embodiments 1-8, wherein each opening of the first plurality of openings and second plurality of openings is formed in a respective one of a first plurality of recessed cavities formed on the first surface of the cartridge body.

10. The cartridge of any one of embodiments 1-9, comprising a first plurality of compressible o-rings each configured to be retained inside a respective one of the first plurality of recessed cavities, and each configured to form a fluid seal pathway between the an opening of a branch channel in the cartridge body and an opening in a respective one of the first plurality of constriction-containing elements.

11. The cartridge of any one of embodiments 1-10, wherein the input port and the output port are disposed on a same surface of the cartridge body.

12. The cartridge of any one of embodiments 1-11, comprising an additional port, distinct from the input port and output port, fluidly connected to one of the input channel and the output channel.

13. The cartridge of embodiment 12, wherein the additional port is sealed by a cap.

14. The cartridge of any one of embodiments 1-13, wherein one of the input channel and the output channel has a diameter of less than 4 mm.

15. The cartridge of any one of embodiments 1-14, wherein one of the input channel and the output channel has a length of less than 15 cm.

16. The cartridge of any one of embodiments 1-15, wherein one of the branch channels has a diameter of less than 4 mm.

17. The cartridge of any one of embodiments 1-16, wherein one of the branch channels has a length of less than 25 mm.

18. The cartridge of any one of embodiments 1-17, wherein the first plurality of branch channels and the second plurality of branch channels each comprise more than four branch channels.

19. The cartridge of any one of embodiments 1-18, wherein the cartridge has an overall fluid throughput of greater than 1 L/min.

20. The cartridge of any one of embodiments 1-19, wherein the cartridge has a length of less than 15 cm.

21. The cartridge of any one of embodiments 1-20, wherein one or more of the first plurality of constriction-containing elements has a length of less than 50 mm.

22. The cartridge of any one of embodiments 1-21, wherein the cartridge comprises one or more of polycarbonate, polypropylene, and polymethyl methacrylate.

23. The cartridge of any one of embodiments 1-22, wherein:
the cartridge body comprises a second surface, the second surface configured to receive a second plurality of constriction-containing elements, each of the second plurality of constriction-containing elements comprising a constriction configured to perturb membranes of cells of the cell suspension to facilitate delivery of the payload to the cells;
each of the first plurality of branch channels opens at a respective one of a third plurality of openings to the second surface of the cartridge body; and
each of the second plurality of branch channels opens at a respective one of a fourth plurality of openings to the second surface of the cartridge body.

24. The cartridge of embodiment 23, comprising a second removable cover configured to hold the second plurality of constriction-containing elements in place against the second surface of the cartridge body, wherein the second removable cover is removable to facilitate removal or replacement of the second plurality of constriction-containing elements.

25. A cartridge for delivering a payload to cells of a cell suspension, the cartridge comprising:
a cartridge body comprising a first surface configured to receive a first plurality of constriction-containing elements and a second surface configured to receive a second plurality of constriction-containing elements, each of the first plurality of constriction-containing elements and the second plurality of constriction-containing elements comprising a respective constriction configured to perturb membranes of cells of the cell suspension to facilitate delivery of the payload to the cells;
a first removable cover configured to hold the first plurality of constriction-containing elements in place against the first surface of the cartridge body and to hold the second plurality of constriction-containing elements in place against the second surface of the cartridge body, wherein the first removable cover comprises an input port configured to receive flow of a cell suspension;
a second removable cover configured to hold the first plurality of constriction-containing elements in place against the first surface of the cartridge body and to hold the second plurality of constriction-containing elements in place against the second surface of the cartridge body, wherein the second removable cover comprises an output port configured to direct flow of the cell suspension out of the cartridge.

26. The cartridge of embodiment 25, wherein the first removable cover and the second removable cover are each slidable over the cartridge body, the first plurality of constriction-containing elements, and the second plurality of constriction-containing elements.

27. The cartridge of any one of embodiments 25-26, wherein the first removable cover and the second removable cover are slidable onto and off of the cartridge body in opposed directions.

28. The cartridge of any one of embodiments 25-27, wherein the first removable cover and the second removable cover are each configured to encircle the cartridge body.

29. The cartridge of any one of embodiments 25-28, wherein the cartridge body comprises:
an input chamber formed in the cartridge body and opening toward a first side of the cartridge body to which the first removable cover attaches, wherein the input chamber is configured to be fluidly connected to and receive flow of the cell suspension from the input port; and
an output chamber formed in the cartridge body and opening toward a second side of the cartridge body to which the second removable cover attaches, wherein the output chamber is configured to be fluidly connected to and direct flow of the cell suspension to the output port.

30. The cartridge of embodiment 29, wherein the cartridge body comprises:
a first plurality of branch channels, wherein each of the first plurality of branch channels intersects the input chamber and opens at a respective one of a first plurality of openings to the first surface of the cartridge body and at a second plurality of openings to the second surface of the cartridge body; and
a second plurality of branch channels, wherein each of the second plurality of branch channels intersects the output chamber and opens at a respective one of a third plurality of openings to the first surface of the cartridge body and at a fourth plurality of openings to the second surface of the cartridge body.

31. The cartridge of embodiment 30, wherein the first removable cover and second removable cover are configured to slide in a direction perpendicular to the first plurality of branch channels and the second plurality of branch channels.

32. The cartridge of any one of embodiments 30-31, wherein the first plurality of branch channels and the second plurality of branch channels are associated with one another in pairs of corresponding branch channels, such that fluid may flow from one branch channel of a pair through a constriction-containing element and into another branch channel of the same pair.

33. The cartridge of embodiment 32, wherein the branch channels of one or more of the pairs of corresponding branch channels are spaced apart from one another in a direction perpendicular to the direction of flow in the input port and output port and perpendicular to the direction of flow of fluid in the branch channels.

34. The cartridge of any one of embodiments 30-33, wherein:
each of the first and second pluralities of openings is formed in a respective one of a first plurality of recessed cavities formed on the first surface of the cartridge body; and
each of the third and fourth pluralities of openings is formed in a respective one of a second plurality of recessed cavities formed on the first surface of the cartridge body.

35. The cartridge of any one of embodiments 29-34, wherein the cartridge body comprises:
a first raised lip configured to form a seal against an inside surface of the first removable cover; and
a second raised lip configured to form a seal against an inside surface of the second removable cover.

36. The cartridge of embodiment 35, wherein:
the first raised lip is configured to retain a first o-ring in a first ridge; and
the second raised lip is configured to retain a second o-ring in a second ridge.

37. The cartridge of any one of embodiments 35-36, wherein:
the first raised lip encircles an opening of the input chamber; and
the second raised lip encircles an opening of the output chamber.

38. The cartridge of any one of embodiments 29-37, wherein one of the input chamber and the output chamber has a width of less than 5 mm.

39. The cartridge of any one of embodiments 30-38, wherein one of the branch channels has a diameter of less than 4 mm.

40. The cartridge of any one of embodiments 30-39, wherein one of the branch channels has a length of less than 25 mm.

41. The cartridge of any one of embodiments 30-40, wherein the first plurality of branch channels and the second plurality of branch channels each comprise more than four branch channels.

42. The cartridge of any one of embodiments 25-41, wherein the cartridge has an overall fluid throughput of greater than 1 L/min.

43. The cartridge of any one of embodiments 25-42, wherein the cartridge has a length of less than 15 cm.

44. The cartridge of any one of embodiments 25-43, wherein one or more of the first plurality of constriction-containing elements has a length of less than 50 mm.

45. The cartridge of any one of embodiments 25-44, wherein the cartridge comprises one or more of polycarbonate, polypropylene, and polymethyl methacrylate.

What is claimed is:

1. A cartridge for delivering a payload to cells of a cell suspension, the cartridge comprising:
   a first plurality of constriction-containing elements, each of the first plurality of constriction-containing elements comprising a respective constriction configured to perturb membranes of cells of the cell suspension to facilitate delivery of the payload to the cells;
   an input port configured to be fluidly connected to receive flow of the cell suspension;
   a cartridge body comprising a first surface, the first surface configured to releasably couple with the first plurality of constriction-containing elements;
   an input channel formed in the cartridge body and configured to fluidly connect the input port to a first plurality of branch channels, wherein each of the first plurality of branch channels connects to the input channel and opens at a respective one of a first plurality of openings to the first surface of the cartridge body;
   an output channel formed in the cartridge body, separate from the input channel, and configured to fluidly connect an output port to a second plurality of branch channels, wherein each of the second plurality of branch channels connects to the output channel and opens at a respective one of a second plurality of openings to the first surface of the cartridge body.

2. The cartridge of claim 1, wherein the first plurality of branch channels and the second plurality of branch channels are oriented in a direction perpendicular to the input channel and the output channel.

3. The cartridge of claim 2, wherein the first plurality of branch channels and the second plurality of branch channels are associated with one another in pairs of corresponding branch channels, such that fluid may flow from one branch channel of a pair through a constriction-containing element and into another branch channel of the same pair.

4. The cartridge of claim 3, wherein the branch channels of one or more of the pairs of corresponding branch channels are spaced apart from one another in a direction perpendicular to the input channel and the output channel and perpendicular to the direction of flow of fluid in the branch channels.

5. The cartridge of claim 1, further comprising a first removable cover configured to releasably couple the first plurality of constriction-containing elements in place against the first surface of the cartridge body, wherein the first removable cover is removable to facilitate removal or replacement of the first plurality of constriction-containing elements.

6. The cartridge of claim 5, wherein the first removable cover is configured to attach to the cartridge body via a sliding connection, such that the first removable cover slides over the first plurality of constriction-containing elements as it is attached to the cartridge body.

7. The cartridge of claim 6, wherein the first removable cover is configured to slide in a direction parallel to the input channel and the output channel.

8. The cartridge of claim 6, wherein the first removable cover is configured to slide in a direction perpendicular to the first plurality of branch channels and the second plurality of branch channels.

9. The cartridge of claim 1, wherein each opening of the first plurality of openings and second plurality of openings is formed in a respective one of a first plurality of recessed cavities formed on the first surface of the cartridge body.

10. The cartridge of claim 9, further comprising a first plurality of compressible o-rings each configured to be retained inside a respective one of the first plurality of recessed cavities, and each configured to form a fluid seal pathway between an opening of a branch channel in the cartridge body and an opening in a respective one of the first plurality of constriction-containing elements.

11. The cartridge of claim 1, wherein the input port and the output port are disposed on a same surface of the cartridge body.

12. The cartridge of claim 1, comprising an additional port, distinct from the input port and output port, fluidly connected to one of the input channel and the output channel.

13. The cartridge of claim 12, wherein the additional port is sealed by a cap.

14. The cartridge of claim 1, wherein at least one of the input channel and the output channel has a diameter of less than 4 mm.

15. The cartridge of claim 1, wherein at least one of the input channel and the output channel has a length of less than 15 cm.

16. The cartridge of claim 1, wherein at least one of the branch channels has a diameter of less than 4 mm.

17. The cartridge of claim 1, wherein at least one of the branch channels has a length of less than 25 mm.

18. The cartridge of claim 1, wherein the first plurality of branch channels and the second plurality of branch channels each comprise more than four branch channels.

19. The cartridge of claim 1, wherein the cartridge has an overall fluid throughput of greater than 1 L/min.

20. The cartridge of claim 1, wherein the cartridge has a length of less than 15 cm.

21. The cartridge of claim 1, wherein one or more of the first plurality of constriction-containing elements has a length of less than 50 mm.

22. The cartridge of claim 1, wherein the cartridge comprises one or more of polycarbonate, polypropylene, and polymethyl methacrylate.

23. A cartridge for delivering a payload to cells of a cell suspension, the cartridge comprising:
a first plurality of constriction-containing elements, each of the first plurality of constriction-containing elements comprising a respective constriction configured to perturb membranes of cells of the cell suspension to facilitate delivery of the payload to the cells;
an input port configured to be fluidly connected to receive flow of the cell suspension;
a cartridge body comprising a first surface, the first surface configured to receive the first plurality of constriction-containing elements;
an input channel formed in the cartridge body and configured to fluidly connect the input port to a first plurality of branch channels, wherein each of the first plurality of branch channels connects to the input channel and opens at a respective one of a first plurality of openings to the first surface of the cartridge body;
an output channel formed in the cartridge body, separate from the input channel, and configured to fluidly connect an output port to a second plurality of branch channels, wherein each of the second plurality of branch channels connects to the output channel and opens at a respective one of a second plurality of openings to the first surface of the cartridge body,
the cartridge body comprises a second surface, the second surface configured to receive a second plurality of constriction-containing elements, each of the second plurality of constriction-containing elements comprising a constriction configured to perturb membranes of cells of the cell suspension to facilitate delivery of the payload to the cells;
each of the first plurality of branch channels opens at a respective one of a third plurality of openings to the second surface of the cartridge body; and
each of the second plurality of branch channels opens at a respective one of a fourth plurality of openings to the second surface of the cartridge body.

24. The cartridge of claim 23, comprising a second removable cover configured to hold the second plurality of constriction-containing elements in place against the second surface of the cartridge body, wherein the second removable cover is removable to facilitate removal or replacement of the second plurality of constriction-containing elements.

* * * * *